(12) United States Patent
Santiago et al.

(10) Patent No.: US 8,414,754 B1
(45) Date of Patent: Apr. 9, 2013

(54) ELECTROPHORETIC SAMPLE ANALYSIS AND APPROACH THEREFOR

(75) Inventors: Juan G. Santiago, Stanford, CA (US); Byoungsok Jung, Stanford, CA (US); Rajiv Bharadwaj, Mountain View, CA (US); Tarun Kumar Khurana, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1545 days.

(21) Appl. No.: 11/755,449

(22) Filed: May 30, 2007

Related U.S. Application Data

(60) Provisional application No. 60/809,500, filed on May 31, 2006.

(51) Int. Cl.
*B01D 57/02* (2006.01)
*G01N 27/447* (2006.01)
*G01N 27/453* (2006.01)

(52) U.S. Cl.
USPC .......................................... 204/549; 204/645

(58) Field of Classification Search .................. 204/549, 204/645
See application file for complete search history.

(56) References Cited

U.S. PATENT DOCUMENTS

| | | | |
|---|---|---|---|
| 3,912,609 A * | 10/1975 | Arlinger | ....................... 204/549 |
| 3,948,753 A | 4/1976 | Arlinger | |
| 4,416,762 A | 11/1983 | Akiyama | |
| 5,800,692 A * | 9/1998 | Naylor et al. | .................. 204/601 |
| 6,905,583 B2 | 6/2005 | Wainright et al. | |
| 7,005,050 B2 | 2/2006 | Burns et al. | |
| 2002/0079223 A1* | 6/2002 | Williams et al. | .............. 204/549 |
| 2004/0108207 A1* | 6/2004 | Kurnik et al. | .................. 204/450 |
| 2005/0121324 A1 | 6/2005 | Park et al. | |

FOREIGN PATENT DOCUMENTS

WO    WO 03/015901    2/2003

OTHER PUBLICATIONS

Jung, B., et al., "On-Chip Millionfold Sample Stacking Using Transient Isotachophoresis", Analytical Chemistry, vol. 78, No. 7, Apr. 1, 2006, p. 2319-2327.*
Xu et al. "Electrokinetic supercharging preconcentration and microchip gel electrophoretic separation of sodium dodecyl sulfate-protein complexes" *Electrophoresis*, 24, 3821-3827 (2003).
Xu et al. "Optimization of the electrokinetic supercharging preconcentration for high-sensitivity microchip gel electrophoresis on a cross-geometry microchip" *Electrophoresis*, 25, 2357-2362 (2004).

(Continued)

*Primary Examiner* — J. Christopher Ball
(74) *Attorney, Agent, or Firm* — Crawford Maunu PLLC

(57) ABSTRACT

Analysis of samples is facilitated. According to an example embodiment, an electrophoresis approach involves electrophoretically stacking and/or separating a sample or samples. An electrolyte and a mixture of one or more samples with another electrolyte are added to a microchannel or capillary. An electric field is applied to stack (and, in some applications, further separate) the one or more samples. Generally, the electric field and electrolyte are used to facilitate isotachophoretic (ITP) stacking. In some embodiments, a further electric field is applied and used with the electrolyte to facilitate subsequent capillary electrophoresis (CE).

45 Claims, 13 Drawing Sheets

OTHER PUBLICATIONS

Xu et al. "Performance of electrokinetic supercharging for high-sensitivity detection of DNA fragments in chip gel electrophoresis" *Electrophoresis*, 24, 3875-3881 (2004).

Woolley et al. "Ultra-high-speed DNA fragment separations using microfabricated capillary array electrophoresis chips" *Proc. Natl. Acad. Sci. USA*, vol. 99, pp. 11348-11352 (Nov. 1994).

Xu et al. "High-sensitivity capillary gel electrophoretic analysis of DNA Fragments on an electrophoresis microchip using electrokinetic injection with transient isotachophoretic preconcentration." Journal of Chromatography A, 990 (2003) 53-61.

Krivankova et al. "Isotachophoresis 17." Methods in Enzymology, 1996, vol. 270, pp. 375-401.

Petr et al. "Capillary isotachophoresis from the student point of view—images and the reality." Journal Sep. Science, 2006, 29, pp. 2705-2715.

Beard. N.R. et al "In-column field-amplified sample stacking of biogenic amines on microfabricated electrophoresis devices." Electrophoresis, 2003. 24(4): p. 732-739.

Jacobson S. et al. "Microchip electrophoresis with sample stacking." Electrophoresis, 1995. 16(4): p. 481-486.

Quirino J.P. et al. "Sample stacking of fast-moving anions in capillary zone electrophoresis with pH-suppressed electroosmotic flow." Journal of Chromatography, 1999. 850(1-2): p. 339-344.

Ross, D. et al. "Microfluidic Temperature Gradient Focusing." Analytical Chemistry, 2002. 74(11): p. 2556-2564.

Wainright A. et al. Preconcentration and separation of double-stranded DNA fragments by electrophoresis in plastic microfluidic devices. Electrophoresis, 2003. 24(21): p. 3784-92.

Wainright A. et al. "Sample pre-concentration by isotachophoresis in microfluidic devices." Journal of Chromatography, 2002. 979(1-2): p. 69-80.

Wang Y. et al. "Million-fold preconcentration of proteins and peptides by nanofluidic filter." Analytical Chemistry, 2005. 77(14): p. 4293-4299.

Yang H. et al. "Sample stacking in laboratory-on-a-chip devices." Journal of Chromatography, 2001. 924(1-2): p. 155-163.

Zhang C.X. et al. "Head-column-field-amplified sample stacking in binary system capillary electrophoresis: A robust approach providing over 1000-fold sensitivity enhancement." Analytical Chemistry, 1996. 68(15): p. 2523-2532.

\* cited by examiner

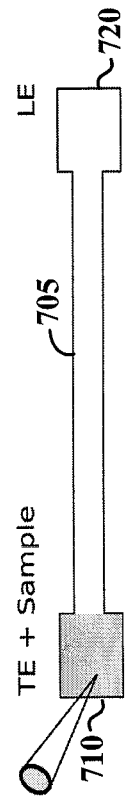
FIG. 7B
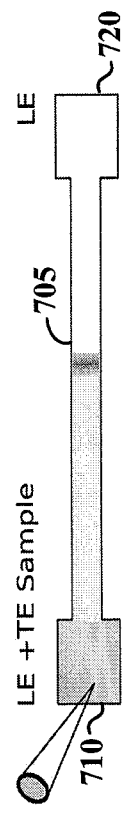
FIG. 7D
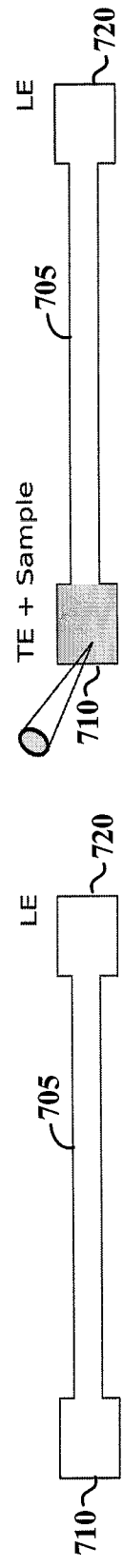
FIG. 7A
FIG. 7C
FIG. 7E
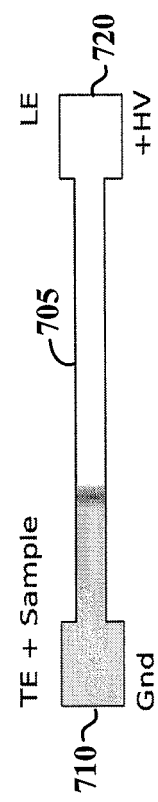
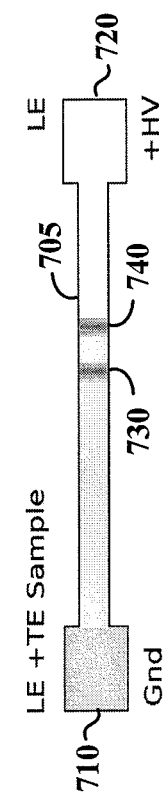

ELECTROPHORETIC SAMPLE ANALYSIS AND APPROACH THEREFOR

RELATED PATENT DOCUMENTS

This patent document claims the benefit, under 35 U.S.C. §119(e), of U.S. Provisional Patent Application No. 60/809,500, filed May 31, 2006 and entitled: "Sample Analysis And Approach Therefor."

STATEMENT REGARDING FEDERALLY-SPONSORED RESEARCH OR DEVELOPMENT

This invention was made with U.S. Government support under contract F30602-00-2-0609 awarded by the Air Force Research Laboratory/IFOJ and contract 0239080 awarded by the NSF; the U.S. Government has certain rights in the invention.

FIELD OF THE INVENTION

The present invention relates generally to sample analysis, and more particularly to electrophoretic sample analysis.

BACKGROUND

Electrophoresis approaches have been long used in the separation and analysis of samples for variety of purposes, such as for identifying a particular substance or for determining the size and type of molecules in a solution. For example, a variety of molecular biology applications have employed electrophoresis to separate proteins or nucleic acids, determine molecular weight, and/or prepare samples for further analysis. In these and other applications, electrophoresis generally involves the movement of an electrically-charged substance (e.g., molecules or ions) under the influence of an electric field. This movement facilitates the separation of a sample from other samples or substances. Once separated, the sample is readily analyzed using an optical or other approach.

A variety of electrophoresis-based approaches are used in connection with different applications to suit the particular needs of the analysis that to be performed. One type of electrophoresis is capillary electrophoresis (CE), which separates ionic samples using charge and frictional forces, generally within a small channel or capillary, using the size-to-charge ratio of the samples to facilitate their respective separation. One particular type of CE that has been the subject of extensive research in recent years is on-chip CE, wherein a small channel or capillary is formed on a microchip. On-chip CE has been useful to facilitate rapid sample separation and reduced sample volumes, and has further been readily integrated with other microfluidic functions. However, the limit of detection (LOD) of on-chip CE systems can be limited by associated small sample volumes and the shallow depth of etched channels (e.g., 10-20 μm), which limits the path length available for imaging a sample or samples in the channel.

In some applications, sample stacking approaches are used with on-chip CE to improve the sensitivity of sample analysis, facilitating the use of less sensitive detection approaches such as electrochemical detection or ultraviolet (UV) absorption. Stacking also facilitates robust injection schemes because the preconcentration of samples, as is associated with stacking, reduces the effective sample injection width (e.g., the width of sample material in a capillary or microchannel).

One type of on-chip stacking involves electromigration-based processes, such as field-amplified sample stacking (FASS), large volume sample stacking, and isotachophoresis (ITP). Electromigration-based sample stacking leverages spatial gradients of electrophoretic velocity of sample analytes as effected by gradients in ion density, mobility, and/or solvent viscosity. In FASS, signal enhancement factors have been generally limited to 1,000-fold using free-standing capillaries, and 100-fold using microchips, prior to demonstration of 1000-fold on-chip FASS. In ITP, charged particles are separated using an electric field to create boundaries or interfaces between materials (e.g., between the charged particles and other materials in a solution). ITP has been combined with CE as a robust, pre-separation sample stacking approach, has been demonstrated using rare earth metals and simple acids, and has been integrated with on-chip CE approaches. ITP generally uses multiple electrolytes, where the electrophoretic mobilities of sample ions are less than that of a leading electrolyte (LE) and greater than that of a trailing electrolyte (TE) that are placed in a microchannel or capillary. Individual species of a sample form narrow zones between the LE and TE and migrate with the same velocity (i.e., "isotacho" means equal velocity). With judicious choice of LE and TE chemistry, ITP is fairly generally applicable, can be accomplished with samples initially dissolved in either or both the TE and LE electrolytes, and (unlike FASS) does not require very low electrical conductivity background electrolytes.

While ITP has been readily implemented and useful for many applications, its implementation has been challenging for a variety of reasons. For instance, one challenging aspect of ITP has been that it requires significant knowledge of the electrophoretic mobilities of sample ions, prior to analysis, to ensure that the TE and LE electrolytes are appropriately chosen. That is, the nature of the TE and LE are relatively important in these prior approaches, to achieve adequate sample separation. In addition, controlling the placement and progression of materials in fluid channels in a manner that facilitates desirable analysis has also been challenging. Moreover, integrated ITP and CE approaches have generally required several steps in the separation and analysis process, and as such can be cumbersome and time consuming. These and other characteristics have been challenging to electrophoresis, isotachophoresis and related applications.

SUMMARY

The present invention is directed to overcoming the above-mentioned challenges and others related to the types of electrophoresis applications discussed above and in other applications. These and other aspects of the present invention are exemplified in a number of illustrated implementations and applications, some of which are shown in the figures and characterized in the claims section that follows.

Various aspects of the present invention are applicable to electrophoretic approaches. Some example embodiments are generally directed to the addition of a mixture including at least one sample and an electrolyte to a microchannel (e.g., in a microchip or capillary), and application of a voltage to isotachophoretically move the sample to facilitate analysis thereof. Certain example embodiments of the present invention are directed to microfluidic devices for carrying out in situ sample stacking and, in some applications, electrophoresis with application of such a mixture involving one or more samples. Other example embodiments are directed to devices and approaches for single-interface isotachophoresis (ITP) applications and their selective integration with electrophoretic separation.

According to another example embodiment of the present invention, an electrophoretic analysis approach involves introducing (e.g., adding) first electrolytes to a microchannel and further introducing a mixture of second electrolytes with at least one type of sample analytes to the microchannel. The first and second electrolytes are selected such that the electrophoretic mobility of at least one of the types of sample analytes is between the respective electrophoretic mobilities of the first and second electrolytes. The at least one type of sample analytes is isotachophoretically arranged by applying an electric field to the microchannel to effect. Once arranged, characteristics of the sample analytes are detected and an output characterizing the detected characteristics is generated. In some applications, an interface is formed between the first electrolytes and the mixture of the second electrolytes with the sample analytes, prior to isotachophoretically arranging the sample analytes. In certain applications, the isotachophoretically arranged sample analytes are further electrophoretically moved and/or separated, prior to the detection of characteristics thereof.

According to another example embodiment of the present invention, a single-channel electrophoresis approach involves adding leading electrolyte material to a single-channel microchannel, and further adding a mixture including a trailing electrolyte material and at least two samples to the microchannel. The leading and trailing electrolyte materials are selected such that their respective electrophoretic mobilities are larger and smaller than the electrophoretic mobilities of the samples. The samples are isotachophoretically stacked by applying an electric field to the microchannel, and the stacked samples are separated by applying an electric field to the microchannel to mitigate the isotachophoretic stacking and facilitate capillary electrophoresis of the stacked samples with the first electrolytes.

In connection with another example embodiment of the present invention, sample analytes are analyzed utilizing a T-microchannel having a main separation channel, a side channel and a reservoir connected to an upstream portion of the main separation channel. Electrolytes of a first type are introduced into a downstream portion of the main separation channel, the electrolytes of the first type having an electrophoretic mobility that is greater than the electrophoretic mobility of the sample analytes. A mixture of electrolytes of a second type with sample analytes is introduced into an upstream portion of the main separation channel using pressure driven flows, the electrolytes of the second type having an electrophoretic mobility that is less than the electrophoretic mobility of the sample analytes. A boundary is formed between the first electrolytes and the mixture at an intersection of the T-microchannel. A voltage difference is applied between the downstream and the upstream portion of the main separation channel to isotachophoretically stack the sample analytes. After applying the voltage difference, the reservoir is filled with electrolytes of the first type and a voltage difference is again applied between the downstream and the upstream portion of the main separation channel to separate the sample analytes.

According to another example embodiment of the present invention, a single-interface electrophoresis approach involves analyzing a sample in a single-channel microchip microchannel having a single main separation channel with wells at opposite ends thereof. A first type of electrolytes are introduced into a portion of the microchannel and, using pressure-driven flow, the separation channel is filled with the first type of electrolytes. A mixture including a second type of electrolytes mixed with at least one type of sample analytes is introduced into one of the wells, where the electrophoretic mobility of sample analytes is between that of the first and second electrolytes (e.g., lower than the first electrolytes and higher than the second electrolytes, where the first and second electrolytes are respectively leading and trailing electrolytes). An electric field is applied across the separation channel to initiate isotachophoretic stacking of the sample analytes. In some applications, after isotachophoretically stacking sample analytes, an electric field is applied across the separation channel to facilitate overspeeding of the sample analytes by an electrolyte. This overspeeding (i.e., the electrophoretic moving of electrolytes to or past the sample) mitigates the isotachophoretic stacking and electrophoretically further arranges the sample analytes via capillary electrophoresis. In some applications involving two or more sample analytes, the capillary electrophoresis separates the two or more sample analytes.

According to another example embodiment of the present invention, a single-channel electrophoresis system includes a separation channel, electrodes at opposite ends of the separation channel and a voltage supply coupled to the electrodes. The separation channel includes a first electrolyte material and a mixture including a second electrolyte material and one or more samples. The electrophoretic mobilities of some or all of the samples are between that of the first and second electrolyte materials (e.g., where the first and second electrolytes are respectively leading and trailing electrolyte materials). The voltage supply applies an electric field to the separation channel via the electrodes to isotachophoretically stack the sample(s). In some applications, subsequent to the isotachophoretic stacking, the voltage supply further applies an electric field to the separation channel to separate the stacked samples by mitigating (e.g., terminating) the isotachophoretic stacking and facilitating capillary electrophoresis of the stacked samples with the first electrolytes.

According to another example embodiment of the present invention, an approach to single-channel isotachophoresis involves isotachophoretically concentrating a sample in a single-channel microchannel. A first electrolyte material is added to the single-channel microchannel, and a mixture that includes a second electrolyte material and the sample is also added to the microchannel. The electrolyte materials are selected such that the electrophoretic mobility of the sample has a value that is between the respective electrophoretic mobility values of the first and second electrolyte materials. The sample is isotachophoretically concentrated by applying an electric field to the microchannel and the concentrated sample is analyzed.

The above summary is not intended to describe each illustrated embodiment or every implementation of the present invention.

BRIEF DESCRIPTION OF THE DRAWINGS

The invention may be more completely understood in consideration of the detailed description of various embodiments of the invention that follows and the accompanying drawings, in which:

FIGS. 7A-7E show a single-channel electrophoresis arrangement and approach at various stages, according to another example embodiment of the present invention;

FIGS. 11A-11C show a microchannel arrangement with three approaches for ITP separation, according to various example embodiments, in which FIG. 11A shows ITP preconcentration with sample ions mixed with trailing electrolyte and added to the microchannel arrangement, FIG. 11B shows ITP preconcentration with sample ions mixed with leading electrolyte and added to the microchannel arrangement, and FIG. 11C shows ITP preconcentration with sample ions separately mixed with leading and trailing electrolyte and added to respective reservoirs of the microchannel arrangement.

Figure 1A:
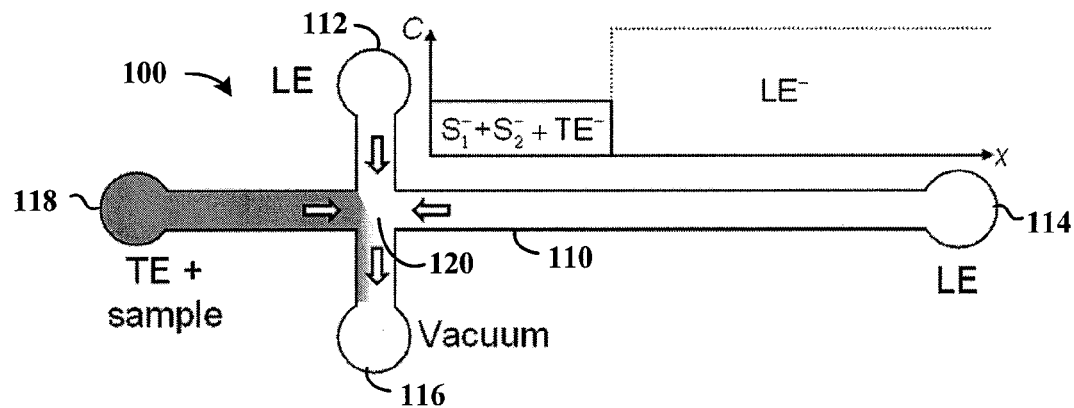
FIGS. 1A-1D show an isotachophoresis/capillary electrophoresis (ITP/CE) arrangement and assay approach at various stages, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments shown and/or described. On the contrary, the intention is to cover all modifications, equivalents, and alternatives falling within the spirit and scope of the invention.

DETAILED DESCRIPTION

The present invention is believed to be applicable to a variety of different electrophoresis processes, devices and arrangements, and certain aspects have been found to be particularly suited for isotachophoresis-based electrophoresis. While the present invention is not necessarily so limited, various aspects of the invention may be appreciated through a discussion of examples using these contexts.

According to an example embodiment of the present invention, a sample is stacked or otherwise arranged for analysis using an isotachophoresis approach. The sample is mixed with an electrolyte and the mixture (e.g., a homogeneous mixture) is added to a separation channel such as a microchip or capillary. A different electrolyte is also added to the separation channel, such that the electrophoretic mobility of the sample (or a portion thereof) has a value that is between the electrophoretic mobilities of the electrolyte in the mixture and the different electrolyte. In this context, the sample may include one or more different sample types such as different proteins, and the arrangement of the sample involves the arrangement of one, two or more samples. A voltage is applied to the separation channel to isotachophoretically move and arrange the sample, and the arranged sample is analyzed (e.g., the sample is identified).

In some embodiments, the sample is first isotachophoretically concentrated or stacked using the above approach, and the concentrated or stacked sample is further separated via capillary electrophoresis using a common or separate voltage (and corresponding electric field) application. Generally, an isotachophoresis approach is first implemented to arrange (e.g., segregate, focus, concentrate or stack) the sample among the electrolytes in the mixture. Electrolytes different than those in the mixture are electrophoretically positioned to overtake (e.g., mix with) the sample to terminate isotachophoretic stacking and initiate capillary electrophoresis. In applications where the sample includes two or more sample types (e.g., two types of molecules such as proteins), the samples are stacked via isotachophoresis and the stacked samples are separated via capillary electrophoresis.

In various example embodiments, a sample as described above is mixed with one or more types of electrolytes to suit different applications. In this regard, the sample is mixed with leading electrolytes, trailing electrolytes, with both leading and trailing electrolytes in separate mixtures, or as a single mixture that includes both leading and trailing electrolytes. In each instance, a voltage is applied to the separation channel to isotachophoretically concentrate or stack the sample or samples. Where appropriate, capillary electrophoresis is further used to separate the concentrated or stacked sample or samples for analysis.

In another example embodiment, a sample is arranged via single-channel isotachophoresis. Leading electrolyte material is added to a single-channel microchannel. A mixture including a trailing electrolyte material and multiple samples is also added to the microchannel, with the electrophoretic mobilities of the leading and trailing electrolyte materials being respectively larger and smaller than the electrophoretic mobilities of one or more of the samples. The samples are then isotachophoretically stacked by applying an electric field to the microchannel.

In various example embodiments, samples that are stacked, separated or otherwise arranged are analyzed using one or more approaches. For instance, some applications involve detecting light from the arranged samples, with the arrangement facilitating the detection, the detection made easier by the concentration of the sample(s) or, where more than one sample is involved, the separation of the sample(s). Similarly, other applications are directed to the detection of electrochemical detection characteristics, using electrodes or other approaches. Still other applications are directed to the detection of ultraviolet (UV) absorption characteristics of the sample(s). These and other detection approaches are readily implemented with and facilitated by the ITP arrangement and, where used, CE separation. Furthermore, these analysis approaches are selectively implemented with any of the example embodiments described herein, including those shown in the figures and described below.

In some embodiments, additional electrolytes are added to one or more portions of a separation channel arrangement as described above to facilitate the separation of the sample analytes (e.g., near the end of an ITP stage and/or beginning of a CE stage of separation). This addition is carried out at one or more stages of the separation approach, and such as between application of voltages where a further electric field is applied as described above.

In some example embodiments, an ITP or integrated ITP/CE approach as described above is further implemented with electroosmotic flow (EOF) suppression to facilitate analysis of the sample. In one implementation, a coating is applied to a wall of the microchannel. For example, using a material such as 0.1% w/v poly(N-hydroxyethylacrylamide) (PHEA) to coat the microchannel, there is a reduction in EOF, relative to that exhibited with an uncoated microchannel. In another implementation, a linear polymer material such as Polyethylene oxide or Polyvinyl pyrrolidone is added to leading and/or trailing electrolytes to suppress electroosmotic flow.

In another example embodiment, an ITP or integrated ITP/CE approach as described above involves the use of a relatively high leading ion concentration (for the leading electrolytes) to facilitate separation and analysis. For example, one application is directed to the use of leading electrolytes having a molar ratio, relative to the sample analytes, of at least about 500:1. Another application is directed to the use of leading electrolytes having a molar ratio, relative to the sample analytes, of at least about 1000:1.

The addition or introduction of the mixture and additional electrolytes to a separation channel is carried out in one or more of a variety of manners. In one example embodiment, a mixture of sample analytes with trailing electrolytes (TE) is injected into a microchannel to initiate ITP stacking. Leading electrolytes (LE) are subsequently injected into the microchannel (e.g., at an intersection of channels). The latter LE ion stream overspeeds TE ions behind the stacked sample zone, terminates ITP, and initiates CE separation. In connection with this example embodiment, it has been discovered that the stacked sample concentration is proportional to the LE concentration, and the concentration increase, CI, increases as the initial sample concentration decreases. It has also been discovered that the stacked sample concentration is a strong function of the TE concentration and the initial sample concentration. In some applications, low conductivity TE zones result in higher TE zone electric fields and therefore faster rates of stacking. High TE zone fields can be correlated with high stacked zone fields, $E_s$. In this regard, this approach, combined with the large effective injection length of the single-interface configuration, can facilitate large sample electric Peclet numbers and efficient stacking that is less susceptible to dispersion. In some implementations, comprehensive multi-species models have coupled fluid flow, current conservation, and convective-diffusion-electromigration conservation to facilitate ITP.

A variety of channel shapes and arrangements are used in connection with various example embodiments. In some applications, this ITP/CE approach is performed using a microchannel with a single linear channel, in other applications with a microchannel having a cross-shaped channel, and in still other applications with a microchannel having a T-shaped or double T-shaped channel, all selectively with one or more additional side channels.

According to another example embodiment of the present invention, and as may be implemented with the above, a microchip single-interface isotachophoresis approach is used to analyze a sample. An interface between first electrolytes having a first electrical conductivity and mixture of sample analytes with second electrolytes having a second electrical conductivity is formed in a microchannel, such as at an inlet or junction. The first electrolytes are selected from electrolytes having an electrophoretic mobility that is greater than that of the sample analytes, and the second electrolytes are selected from electrolytes having an electrophoretic mobility that is less than that of the sample analytes. In this context, the interface is generally a single solution/solution interface, between a first solution of the first electrolytes and a second solution including both the second electrolytes and the sample analytes. Moreover, the precise electrophoretic mobilities of the electrolytes and sample analytes need not necessarily be known a priori; ensuring that the relative mobilities discussed above hold is sufficient. This approach is applicable, for example, for use with a single-channel microchannel (e.g., a generally linear channel), or with a microchannel having a main channel and an additional channel that intersects the main channel, such as in a "Y," "T" or "X" shape.

In another example embodiment, an interface between the first electrolytes and the mixture with the sample analytes is formed at an intersection of a cross-shaped microchannel as follows. The first electrolytes are introduced into the downstream portion of a main separation channel and a first side channel, and a mixture of the second electrolytes and sample analytes is introduced into the upstream portion of the main separation channel using pressure driven flows. A voltage difference is applied between the downstream and upstream portions of the main separation channel, and a voltage difference is subsequently applied between the downstream portion of the main separation channel and the first side channel to isotachophoretically stack the sample analytes.

In another example embodiment, a boundary between the first electrolytes and the mixture with the sample analytes is formed at a junction of T-channel microchannel as follows. The first electrolytes are introduced into a downstream portion of a main separation channel, and a mixture of the second electrolytes and sample analytes is introduced into an upstream portion of the main separation channel using pressure driven flows. A voltage difference is applied between the downstream and the upstream portions of the main separation channel, a reservoir connected to the upstream portion of the main separation channel is replaced with the first electrolytes, and a voltage difference is again applied between the downstream and the upstream portion of the main separation channel to isotachophoretically stack the sample analytes.

In yet another example embodiment, an interface between first electrolytes and sample analytes in a mixture with second electrolytes is formed at an inlet of an upstream portion of a main separation channel of T-shaped microchannel (a "T-microchannel"). The first electrolytes are introduced into the main separation channel and a side channel of the T-microchannel, and a reservoir connected to an inlet of an upstream portion of the main separation channel is filled with the mixture of the second electrolytes and sample analytes. A voltage difference is applied between downstream and upstream portions of the main separation channel, and another voltage difference is subsequently applied between the downstream portion of the main separation channel and the side channel, to isotachophoretically stack the sample analytes.

A variety of electrolytes are used as and/or with the first and second, or leading and trailing, electrolytes as discussed above. In some applications, one or both of the first and second electrolytes include linear polymers and are implemented with gel electrophoresis. In other applications, the first and second electrolytes include materials such as those described in the Experimental Data section below.

For general information regarding approaches to sample analysis, and for specific information regarding approaches to analysis using ITP and CE in accordance with one or more example embodiments of the present invention, reference may be made to Byoungsok Jung, Rajiv Bharadwaj and Juan G. Santiago, "On-Chip Millionfold Sample Stacking Using Transient Isotachophoresis," Anal. Chem. 2006, 78, 2319-2327, and to Byoungsok Jung, Yonggang Zhu, and Juan G. Santiago, "Detection of 100 aM Fluorophores Using a High-Sensitivity On-Chip CE System and Transient Isotachophoresis," Anal. Chem. 2007, 79(1), pp 345-349, which are fully incorporated herein by reference.

Turning now to the figures, FIGS. 1A-1D show an isotachophoresis/capillary electrophoresis (ITP/CE) arrangement and assay approach at various stages, according to an example embodiment of the present invention. Each of FIGS. 1A-1D includes an inset showing concentration (C) over distance (x) at each stage, involving two samples $S_1$ and $S_2$ (e.g., referred to as sample analytes, or sample ions), leading electrolytes (ions) and trailing electrolytes (ions), respectively indicated as LE and TE as consistent with the above.

Beginning with FIG. 1A, a microchannel arrangement 100 including a cross-channel microchannel 110 is used with a single-interface approach to facilitate ITP/CE. The cross-channel microchannel 110 has four channel portions at upper, right, lower and left locations, respectively including a side channel reservoir 112, separation channel reservoir 114, sample waste reservoir 116 and sample reservoir 118. A glass surface of the microchannel 110 is pretreated (e.g., washed) using 1.0 M HCl for about 15 min, and flushed with 0.1% w/v PHEA solution for about 15 min.

After flushing, the microchannel 110 is loaded with sample analytes, LE and TE as shown in FIG. 1A. A relatively high conductivity LE buffer is loaded into the side channel reservoir 112 and separation channel reservoir 114. A mixture including sample analytes and a low conductivity TE buffer is then loaded in the sample reservoir 118. Generally, the LE buffer responds faster to applied electric fields, relative to the TE buffer.

A single interface TE/LE boundary is formed at a cross-intersection 120 of the cross-channel microchannel 110 by applying a vacuum for about 10 seconds at the sample waste reservoir 116. Pressure-driven flows are represented by arrows near the cross-intersection 120. As shown in the inset of FIG. 1A, a mixture of sample analytes and trailing electrolytes is generally located at a portion of the microchannel 110 near the sample reservoir 118, and the leading electrolytes are generally located at a portion of the microchannel 110 near the separation channel reservoir 114.

Figure 1B:
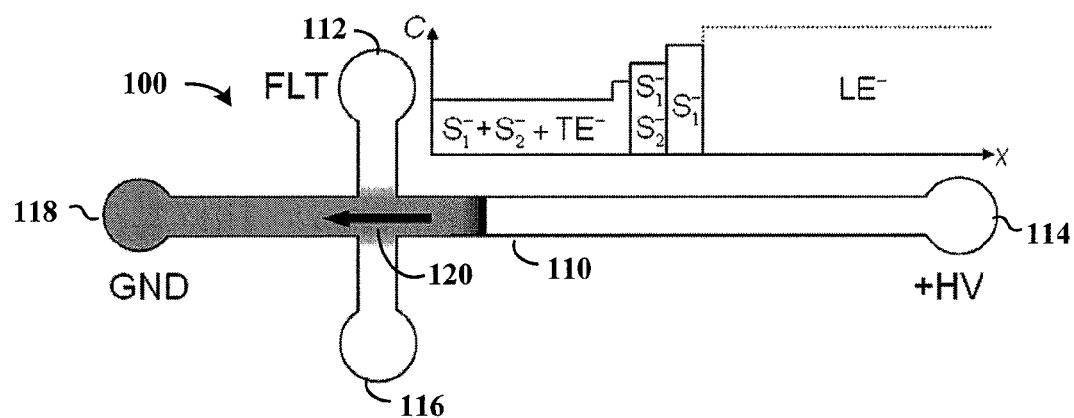

Once the TE/LE boundary is established, an electric potential (e.g., about 2 kV) is applied at the separation channel reservoir 114 and the sample reservoir 118 is grounded, forming an east-to-west electric field as represented in FIG. 1B by a horizontal arrow. This electric field initiates both electrophoretic migration of sample and trailing ions into the separation channel reservoir 114, and ITP sample stacking of the sample to facilitate thereof. Referring to the inset of FIG. 1B, partial separation (i.e., moving boundary electrophoresis) is shown. Viewing FIG. 1B from right to left, leading ions are near the separation channel 114, partially separated sample ions $S_1$ are next to the leading ions, a mixture of sample ions $S_1$ and $S_2$ is next, followed by a mixture of sample ions $S_1$ and $S_2$ with trailing ions nearer the sample reservoir 118.

Figure 1C:
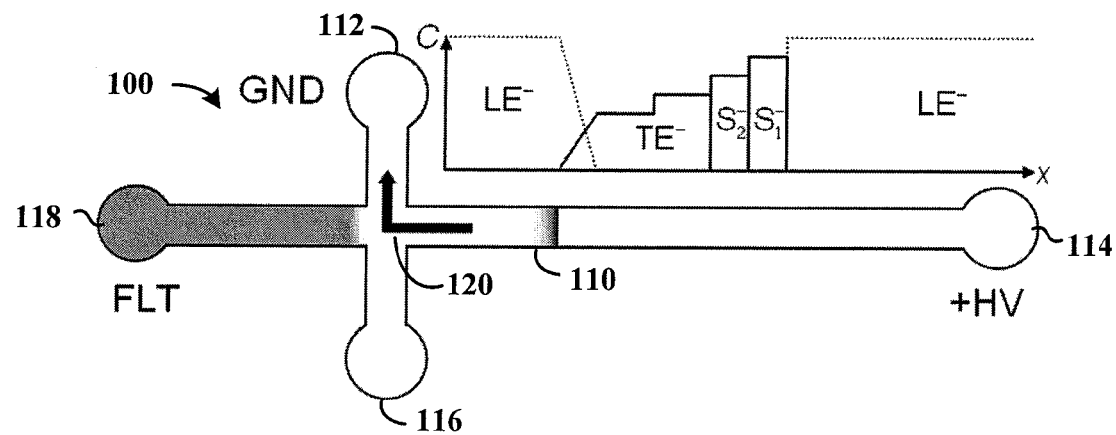

At FIG. 1C, the electric field is switched toward the side channel reservoir 112 by floating the sample reservoir 118 and grounding the side channel reservoir 112. In this step, leading ions are injected into the separation channel 114 to terminate the ITP mode. Referring to the inset in FIG. 1C, the samples $S_1$ and $S_2$ are separated, with leading ions at both (lateral) ends of the microchannel 110 at the sample and separation channel reservoirs 118 and 114, and trailing ions between the sample ions and the leading ions near the sample reservoir 118. Although the stacked sample zone is now well downstream of the intersection 120 as represented in the inset of FIG. 1C (e.g., about 5 to 20 mm downstream), the leading ions have overtaken first trailing ions (e.g., by overspeeding the trailing ions) and then sample ions in the separation channel 114. This replacement of TE with LE effects an electrolyte exchange, terminating ITP stacking and initiating CE separation.

Figure 1D:
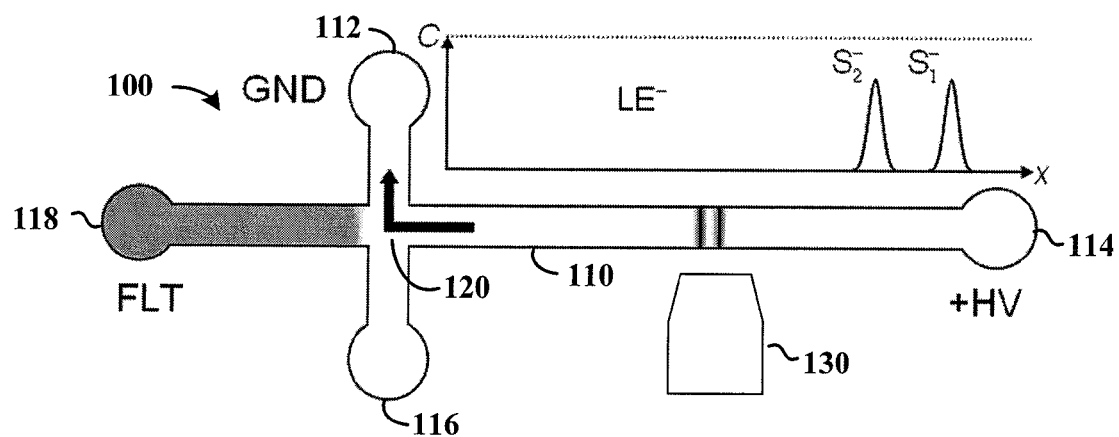

In FIG. 1D, CE separation is continued to facilitate the downstream separation of the sample ions $S_1$ and $S_2$ in nearly homogeneous leading electrolytes (with any remnant of trailing electrolytes not shown), as represented in the inset of FIG. 1D. These separated peaks are detected using a detector arrangement 130, such as an epifluorescent microscope and a CCD (charge-coupled device) camera. This single-interface ITP/CE separation approach facilitates a relatively long effective injected sample plug length and a desirable sample stacking ratio. Further, separation can be achieved without necessarily involving manual buffer exchange steps (e.g., as employed by Xu, Z. Q.; Nishine, T.; Arai, A.; Hirokawa, T. *Electrophoresis* 2004, 25, 3875-3881). In some applications, this separation is accomplished using a standard four-well chip and without necessarily implementing feedback control with injections (e.g., such as the five-well chip and feedback control used by Wainright, A.; Nguyen, U. T.; Bjornson, T.; Boone, T. D. *Electrophoresis* 2003, 24, 3784-3792).

In connection with one or more example embodiments, and as may be implemented with an approach as shown, for example, in FIG. 1A-FIG. 1D, the intensity of detected samples separated using an ITP/CE approach is normalized. For instance, in various applications, the concentration of sample ions can change six orders of magnitude during the ITP stacking process. Since the dynamic range of light detectors such as CCDs or PMTs (photomultiplier tubes) is limited, simultaneous detection of both the initial and stacked sample intensities has been difficult in a single experiment. The diluted sample signal can be below the LOD (limit of detection) of the system, while that of a stacked sample may saturate the detector. To normalize intensity, a quantitative (and calibrated) imaging technique is used as follows.

The measured sample concentration, C, is represented by the following concentration equation $$C = C_{flat} \frac{I_{raw} - I_{bg}}{I_{flat} - I_{bg}}, \qquad \text{(concentration)}$$

where $C_{flat}$ is the known concentration of highly concentrated sample analyte for the flatfield measurement, and $I_{raw}$, $I_{flat}$, and $I_{bg}$ are respectively the signal intensities of stacked sample, flatfield, and background without sample (the latter with shutter open and illumination as normal). The flatfield image is obtained by imaging microchannels filled with a generally homogenous concentration of dye (e.g., with a molar concentration 1E3 to 1E5 times higher than (unstacked) initial sample concentration). In some applications, the microchannel walls are treated with hydrophilic polymers to reduce or mitigate dispersion due to EOF (electroosmotic flow) mismatch.

In various embodiments, one or more of the electric field, injection time, and detector location is varied with an ITP/CE approach to facilitate different detection characteristics. In some applications, these parameters are varied to suit one or more of sample type or types, microchannel type, available leading or trailing electrolytes or desired analysis approach. The following describes approaches for setting such parameters for various example embodiments.

In some embodiments, the voltage scheme used with an ITP/CE approach (e.g., as described with FIGS. 1A-1D) is tailored to a particular chip and detection system used with the microchannel arrangement (e.g., 110) in which a sample or samples are separated. For certain implementations, parameters including the applied electric field strength and the duration of the stacking step (e.g., as shown in FIG. 1C) are set to facilitate desirable stacking and separation.

Figure 2:
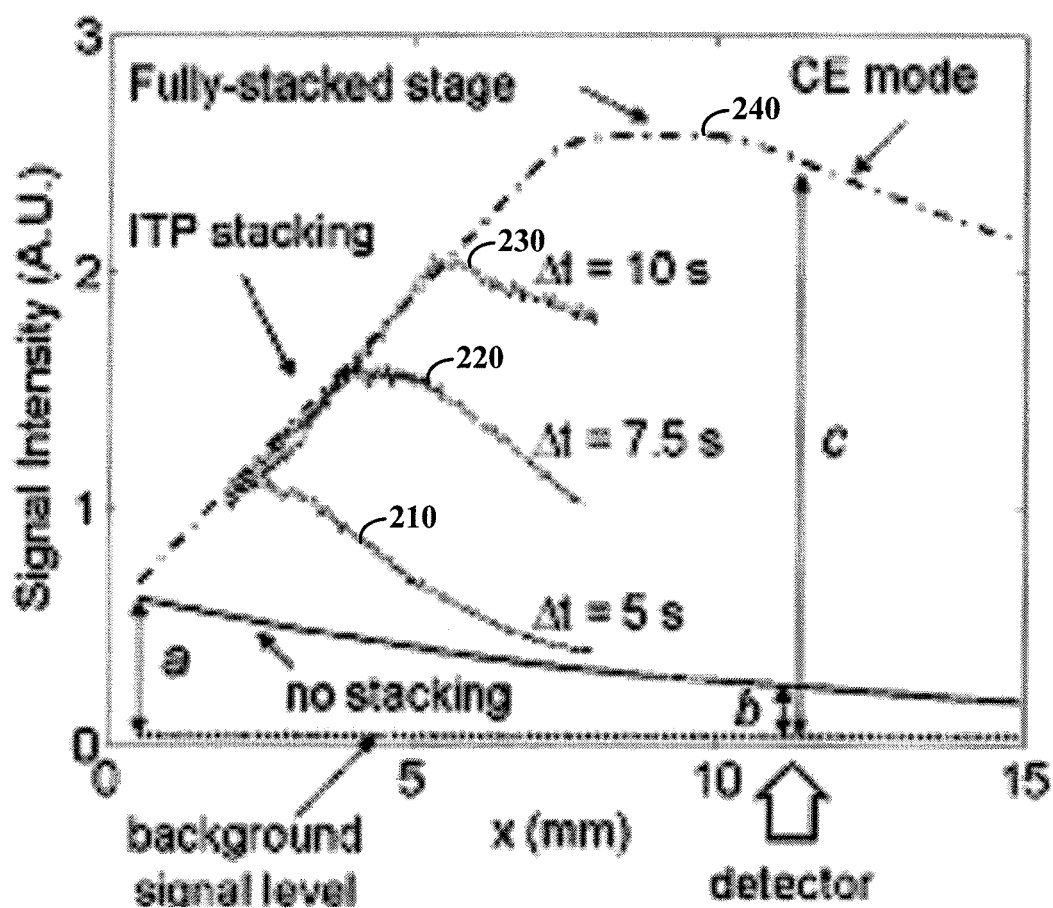
FIG. 2 shows a schematic and various measurements of example signal intensity changes in ITP/CE for a sample analyzed in accordance with one or more example embodiments of the present invention.

FIG. 2 shows plots of example curves of concentration (e.g., maximum) versus separation channel location for an ITP/CE approach, in connection with example embodiments of the present invention. Several traces of actual data are overlaid for reference, as is the relative location of an example detector. For these example embodiments, the applied field and initial sample concentration are respectively 110 V/cm and 100 nM, LE and TE are respectively 50 mM NaCl and 5 mM HEPES, and the duration of the stacking step (ITP) is varied between 5 and 10 s. The original upstream sample intensity is shown at a, the intensity of analyte detected at the downstream location for no stacking conditions is shown at b, and the intensity of the stacked analyte detected downstream is shown at c. In the ITP mode, sample peak signal intensity first increases approximately linearly and eventually saturates, as shown with plots referenced as ITP stacking for times of 5, 7.5 and 10 seconds respectively for plots 210, 220 and 230. Upon initiation of the CE mode, sample concentration scales as the square root of time (and $x^{0.5}$) due to diffusion, as shown with plot 240. As shown, the achievable concentration (maximum) is set or limited by the effective injected sample length as determined by the duration of the ITP step.

In other example embodiments, the injection time of sample analytes is set to suit particular applications relative to conditions such as type of sample, detector location and microchannel size or layout. In general, the injection duration is used to set the separation mode signal position, where a longer sample injection duration is used to push the separation mode signal downstream (e.g., further to the end of the separation channel 114 in FIG. 1D). The injection duration is set sufficiently long enough to facilitate an appropriately-timed termination of ITP (i.e., to ensure full sample stacking), yet not too long to push the separation mode signal position too far into the separation channel. In this regard, the sample injection duration is set to facilitate desirably high resolution and correspondingly low signal-to-noise ratio (SNR). For example, for shorter separation channels, a relatively short injection time is used to allow ample time for separation of the sample. For longer separation channels, longer injection times can be used as more distance is available for separation (e.g., with a sample detector placed relatively far downstream in the separation channel). For instance, one application facilitates desirable stacking and separation using a 40 second sample injection/ITP duration using a nominal electric field of 220 V/cm and a detection point that is about 30 mm downstream into a separation channel.

Figure 3A:
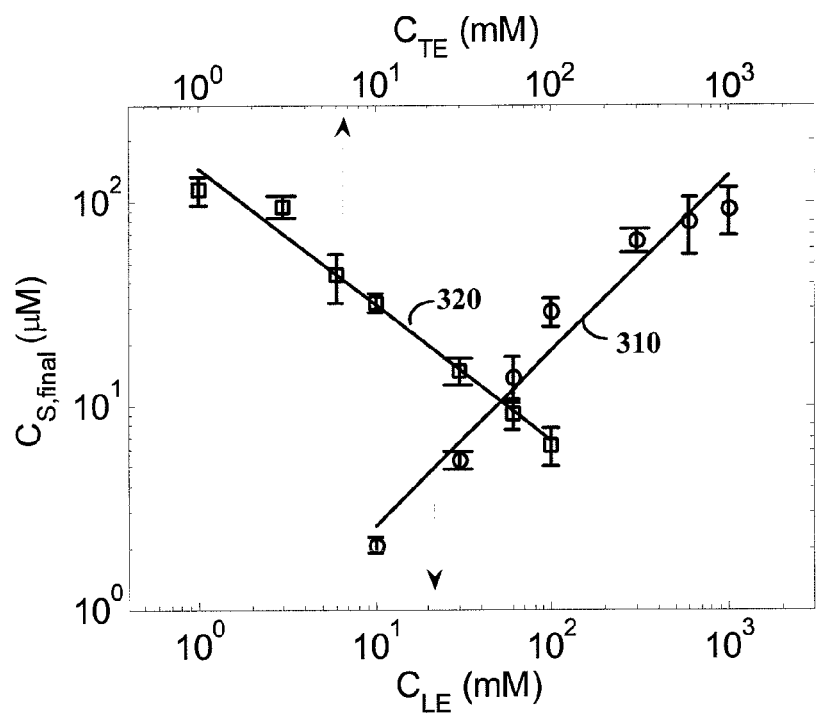
FIG. 3A shows parametric variation of initial concentration profile, according to another example embodiment of the present invention.
Figure 3B:
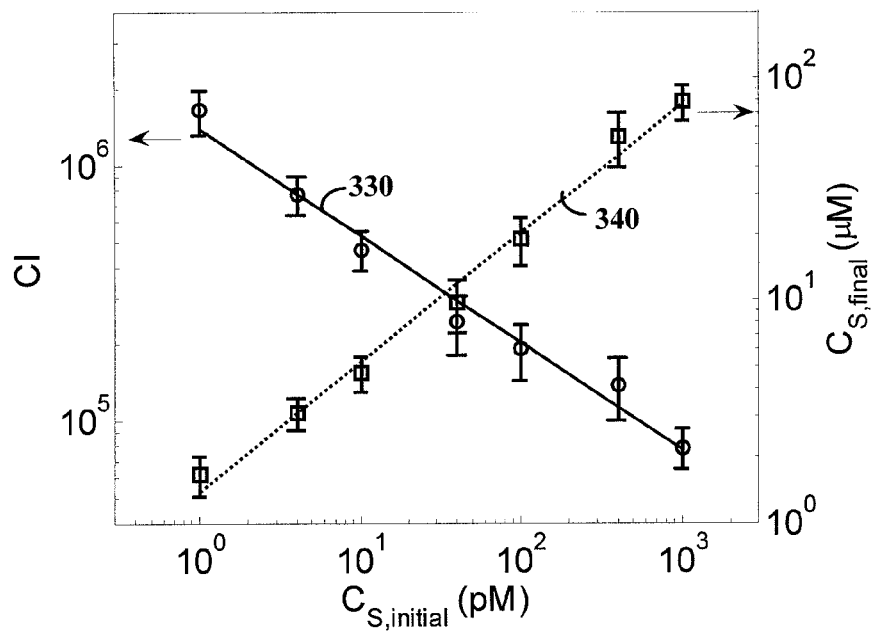
FIG. 3B shows parametric variation of initial concentration profile, according to another example embodiment of the present invention.

FIG. 3A and FIG. 3B are plots showing the effects of LE concentration (using NaCl), $C_{LE}$, and TE concentration (using HEPES), $C_{TE}$ and initial concentration of a sample (using alexa fluor), $C_{S,initial}$ on sample stacking, with a nominal applied field of about 220 V/cm, as may be implemented in accordance with one or more example embodiments herein. Fluorescent signals are detected using a viewing area of about 3.0 mm by 0.3 mm in the object plane at a point that is about 30 mm downstream from the intersection in a cross-channel microchannel, such as that shown in FIG. 1D. All signals reach a fully stacked state (i.e., maximum concentration increase) within this distance from the intersection and during the ITP/CE separation. The exposure time and frame rate are respectively set at 10 ms and 20 frames per second. Cross-section-area-averaged axial intensity profiles are normalized using, for example, an approach as discussed above and shown with the equation for concentration, C, above.

Referring to FIG. 3A, the leading ion concentration, $C_{LE}$, is shown on the horizontal axis and plotted in plot 310 against the final (e.g., maximum) stacked sample concentration, $C_{S,final}$ on the vertical axis at $C_{LE}$ concentrations varying between 10 mM and 1M. The error bars reflect 95% confidence intervals as determined from three realizations of each condition. Here, the TE concentration is fixed at a nominal value of about 5 mM HEPES. The TE solution includes 1 nM alexa fluor 488 as a sample analyte. The associated LE-to-TE conductivity ratios are between about 13.9 and 1.21E3. The stacked sample concentration is nearly directly proportional to the concentration of LE (with a regression coefficient, $R^2$, of 0.95 used for a linear fit).

FIG. 3A also shows the effect of $C_{TE}$ on ITP stacking in plot 320, with $C_{TE}$ plotted on the horizontal axis against the final (e.g., maximum) stacked sample concentration, $C_{S,final}$, on the vertical axis at various $C_{TE}$ concentrations between 1 mM and 100 mM (using a regression coefficient, $R^2$, of 0.97). The LE concentration is fixed at 1 M NaCl, and $C_{S,initial}$ is fixed at 1 nM. The associated LE-to-TE conductivity ratios are between 66.2 to 6.01E3.

In some embodiments, relative to the above discussion regarding FIG. 3A, a high LE-to-TE conductivity ratio (associated with low TE concentrations) is used to increase the electric fields in the TE zone and the stacked sample zones of a microchannel. The high electric field in the TE zone is used to facilitate fast stacking dynamics, by establishing a high electrophoretic flux of the sample from the TE zone to the stacked sample zone. In some applications, high $E_\delta$ is used to facilitate high electric Peclet numbers, and therefore high $C_{S,final}$, as the stacking process is less susceptible to dispersion in accordance with the following equation:

$$Pe_s = \frac{E_\delta v_s}{D}\left(\frac{l}{Cl}\right). \quad \text{(Electric Peclet number)}$$

FIG. 3B shows example plots of $C_{S,initial}$, varied from 1 pM to 1 nM, against CI (concentration increase, at plot 330) and $C_{S,final}$ (plot 340), with CI increasing as $C_{S,initial}$ decreases, and with $C_{S,final}$ increasing with increasing $C_{S,initial}$. The LE and TE concentrations are respectively fixed at about 1 M NaCl and 5 mM HEPES. The LE-to-TE conductivity ratio is kept constant at about 1.27E3 (113 mS/cm for LE and 89.0 µS/cm for TE) for all cases to decouple the results from the effect discussed above (i.e., the dependence of the TE zone electric field and $E_\delta$ on LE-to-TE). The plots respectively use regression coefficients, $R^2$, of 0.97 and 0.98.

In various example embodiments, the width, δ, and area, $A_p$, of sample analyte peaks is controlled or set by selecting LE and TE concentration, with δ decreasing as $C_{LE}$ is increased. In some implementations, a relatively higher $C_{LE}$ used to facilitate a relatively larger stacking ratio and narrow focusing of sample analytes. For higher $C_{LE}$ values, a higher fraction of the total voltage drop is taken along the length of the TE region, increasing the flux of sample into the sample zone. This causes the peak to have lower migration velocity and higher stacking ratio. For increased $C_{LE}$, peak widths therefore have a longer time to grow before being detected at the (fixed) detection point 30 mm downstream.

In other implementations, a relatively higher $C_{TE}$ is used to facilitate decrease in δ, using higher conductivity in the TE/sample zone to lower the TE/sample zone electric field and decrease the rate of stacking, thus increasing the time (and distance) to reach the fully-stacked state. For the fully-stacked states, the widths of the sample zone are narrower for high $C_{TE}$ as the sample peak has had less time to accumulate width. This effect and the lower final concentration value are used to produce lower peak areas for higher $C_{TE}$.

In other example embodiments, trace analytes are detected using ITP stacking, without necessarily implementing CE separation. In one implementation, an initial sample concentration of 100 fM of alexa fluor 488 dye is used with LE of 1 M NaCl and TE of 5 mM HEPES buffer. A 10× objective (N.A. of 0.4) with viewing dimensions of 1.2 by 0.1 mm in the object plane is used to image the sample. A brief (e.g., 2 min) sample stacking step is used to facilitate the detection of the 100 fM analyte concentration with a signal-to-noise ratio (SNR) of about 11 and a measured concentration increase, CI, of about 2E6-fold. In another implementation, a similar approach is used with bodipy samples, with an applied field of about 280 V/cm, with the sample mixture diluted by a factor of about 1E5 (1 pM solutions each of alexa fluor 488 and bodipy) and apply a current single-interface ITP/CE approach as described, for example, with FIGS. 1A-1D above.

FIGS. 4A-4F show an arrangement and approach for T-channel ITP/CE analysis at various stages, according to another example embodiment of the present invention. At FIG. 4A, a T-channel microchannel 400 with a main separation channel 405 is treated to suppress EOF, leading electrolytes (LE) are added at an east reservoir 420 (or, in some applications, to the entire microchannel 400), and a mixture of trailing electrolytes (TE) with samples is added at a west reservoir 430. A vacuum is drawn at a north reservoir 410 to form a TE/LE boundary at a position 440 in the microchannel 400 (near an intersection of the north, east and west reservoirs).

Figure 4A:
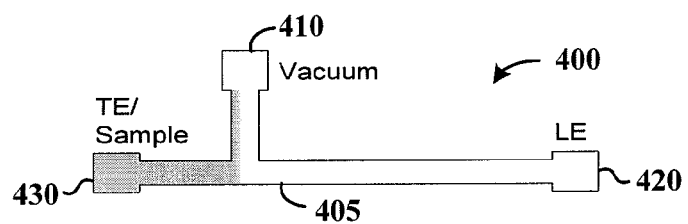
FIGS. 4A-4F show an arrangement and approach for T-channel ITP/CE analysis at various stages, according to another example embodiment of the present invention.
Figure 4B:
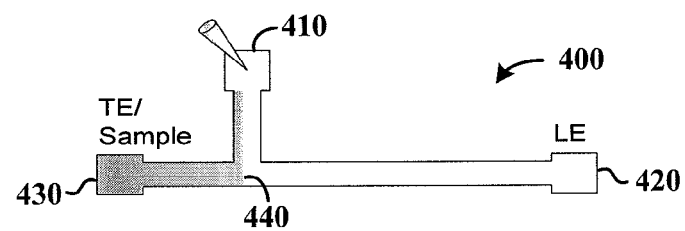

In FIG. 4B, the vacuum is turned off and the north reservoir 410 is filled with LE to a level that is about equal to the amount of material in the east and west reservoirs 420 and 430, respectively. The amount of LE added to the north reservoir 410 is selected to reduce or eliminate any flow due to pressure head differences between the north and east or west reservoirs 420 and 430, respectively.

Figure 4C:
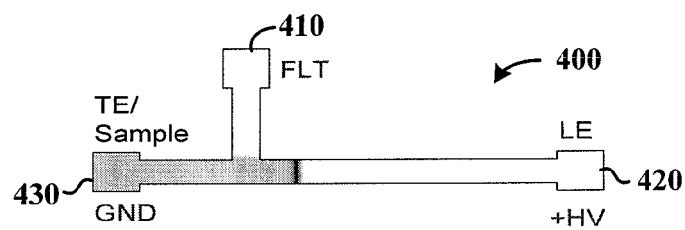
Figure 4D:
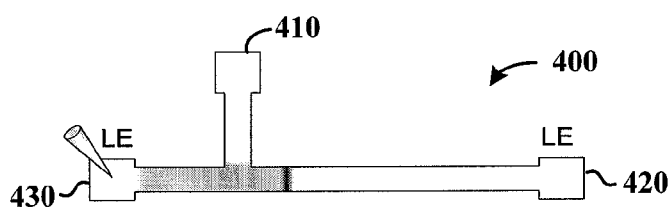

In FIG. 4C, a high voltage is applied at the east reservoir 420 and the west reservoir 430 is grounded while the potential at the north reservoir 410 is floated to initiate ITP stacking. Sample anions electromigrate toward the anode as EOF is suppressed. After the samples have been stacked or at least partially stacked, the west reservoir 430 is filled in FIG. 4D with LE by, for example, adding LE to the west reservoir or replacing material in the west reservoir with LE.

Figure 4E:
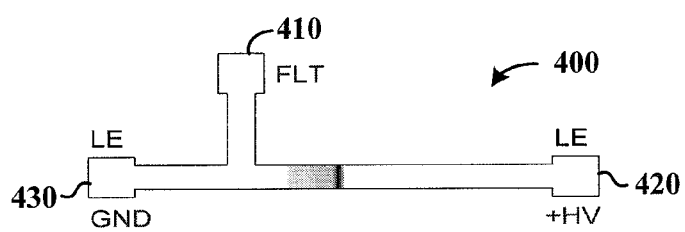
Figure 4F:
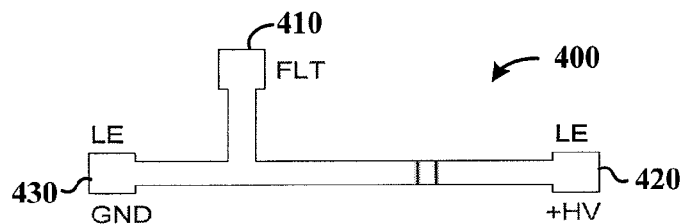

In FIG. 4E, an electric field is activated again in the main separation channel 405 by applying a high voltage at the east reservoir 420, grounding the west reservoir 430 and floating the potential at the north reservoir 410. This field activation injects LE ions behind the sample and initiates CE, with ITP stacking continuing until the LE ions overtake the TE and sample ions. As shown in FIG. 4F, the samples are separated further downstream towards the east reservoir 420 as sample ions electromigrate in nearly homogeneous LE electrolytes (with any remnant of TE not shown for illustrative purposes).

FIGS. 5A-5E show an arrangement and approach for various stages of another T-channel ITP/CE analysis approach, according to another example embodiment of the present invention. Beginning with FIG. 5A, a T-channel microchannel arrangement 500 includes north, east and west reservoirs 510, 520 and 530 respectively, with a main separation channel 505. The microchannel arrangement 500 is filled with LE by filling the east and north reservoirs 520 and 510 with LE (e.g., with solutions drawn in from the west reservoir 530 with a vacuum).

Figure 5A:
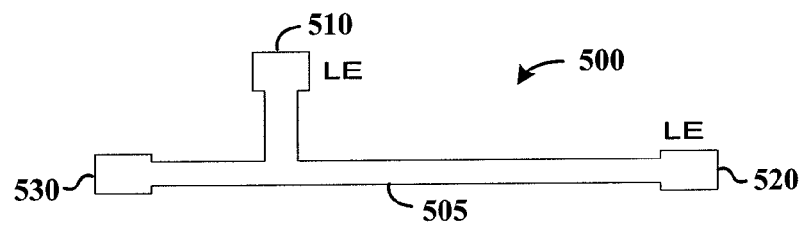
FIGS. 5A-5E show an arrangement and approach for various stages of another T-channel ITP/CE analysis approach, according to another example embodiment of the present invention.
Figure 5B:
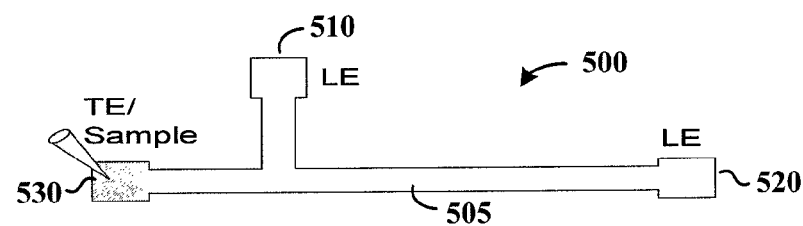
Figure 5C:
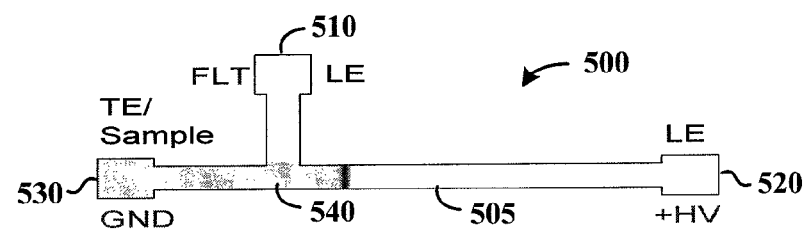

At FIG. 5B, the west reservoir 530 is filled with a mixture of TE and sample analytes. A TE/LE boundary is formed at 540 in the vicinity of the west reservoir as shown in FIG. 5C using ITP stacking, initiated by applying high voltage and ground at the east and west reservoirs 520 and 530, respectively, and floating the north reservoir 510. Sample anions electromigrate toward the anode as EOF is suppressed.

Figure 5D:
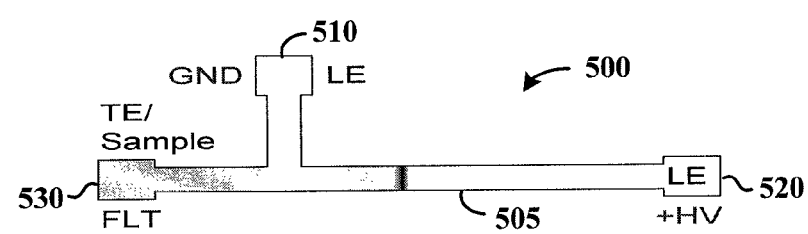

The electric field is switched in FIG. 5D, after adequate sample stacking (i.e., the stacking front passes the T junction 505), toward the north reservoir 510 by grounding the north reservoir and floating the west reservoir 530. This field switch injects LE ions behind the sample and initiates CE. ITP stacking continues until the LE ions overtake the TE and sample ions.

Figure 5E:
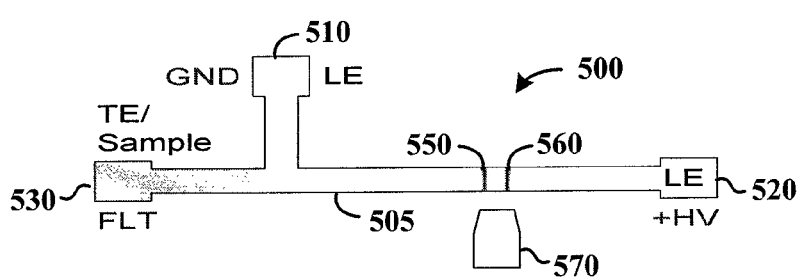

At FIG. 5E, the separation of samples continues with the field initiated at FIG. 5D, with separation occurring downstream with sample ions 550 and 560 electromigrating in nearly homogeneous LE electrolyte (with any remnant of TE not shown). The separated samples 550 and 560 are readily imaged via a detector 570 adjacent the separation channel in the T-microchannel arrangement 500.

FIGS. 6A-6F show a single-channel electrophoresis arrangement 600 and approach for ITP/CE at various stages, according to another example embodiment of the present invention. Beginning with FIG. 6A, the arrangement 600 includes west and east wells (e.g., reservoirs) 610 and 620, at ends of a main separation channel 605 that extends uninterrupted (i.e., without side channels) between the wells. Leading electrolyte (LE) is filled in the arrangement 600 using pressure driven flows (e.g., facilitated by a vacuum at the west well 610).

Figure 6A:
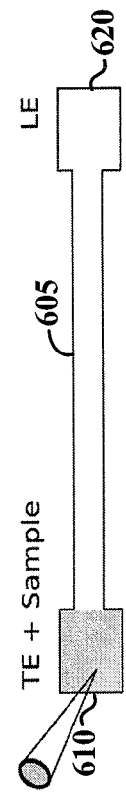
FIGS. 6A-6F show a single-channel electrophoresis arrangement and approach at various stages, according to another example embodiment of the present invention.
Figure 6B:
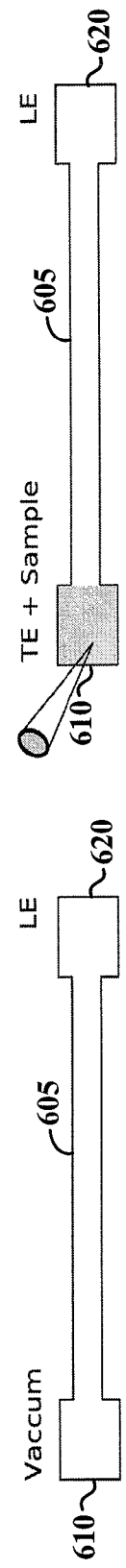
Figure 6C:
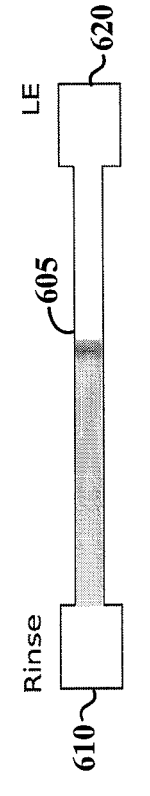

At FIG. 6B, the west well 610 has been rinsed and is filled with mixture of trailing electrolyte and samples. After the mixture of TE and the samples has been filled, into the downstream well 610, an electric field is applied to the separation channel 605 to initiate isotachophoretic stacking at FIG. 6C, using a high voltage applied at the east well 620 while grounding the west well 610.

Figure 6D:
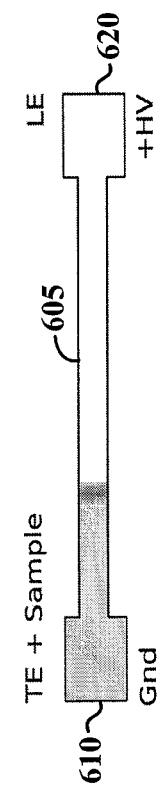
Figure 6E:
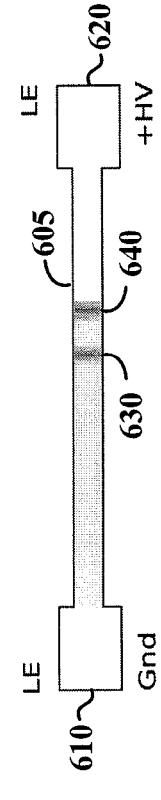
Figure 6F:
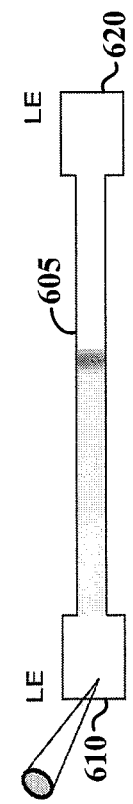

After a steady state has been reached, the electric field is removed (voltage is turned off) at FIG. 6D, and the west well 610 is emptied and rinsed. At FIG. 6E, leading electrolyte (LE) is filled in the west well 610. An electric field is again applied at FIG. 6F, with a high voltage applied at the east well 620 and the west well 610 grounded, to induce separation of the samples 630 and 640.

FIGS. 7A-7E show a single-channel microchannel electrophoresis arrangement 700 and approach at various stages, according to another example embodiment of the present invention. Beginning with FIG. 7A, the single-channel electrophoresis arrangement 700 includes west and east wells 710 and 720 at opposite ends of a separation channel 705. Leading electrolyte is added to the separation channel 705 from one or both wells using, for example, pressure driven flow to fill the separation channel.

At FIG. 7B, the west well 710 is rinsed and a mixture of trailing electrolyte and samples is added to the west well. At FIG. 7C, an electric field is used to initiate isotachophoretic stacking in the separation channel 705 by applying a high voltage to the east well 720 and grounding the west well 710.

Referring to FIG. 7D, the high voltage is turned off after a steady state has been reached, and leading electrolyte is added to the east well 710. At FIG. 7E, an electric field is reapplied across the separation channel by applying a high voltage to the east well 720 and grounding the west well 710 to terminate the isotachophoretic mode and induce separation in the sample ions 730 and 740.

FIGS. 8A-8D show another single-channel electrophoresis arrangement 800 and approach at various stages using a mixture of leading and trailing electrolyte with samples, according to another example embodiment of the present invention. Beginning with FIG. 8A, the arrangement 800 includes west and east wells 810 and 820 on opposite ends of a separation channel 805. Leading electrolyte is filled in the arrangement 800 via one or both of the west and east wells 810 and 820, and flowed into the separation channel using pressure driven flow.

Figure 8B:
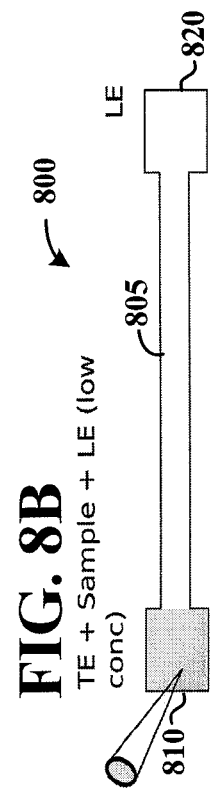
FIGS. 8A-8D show a single-channel electrophoresis arrangement and approach at various stages, according to another example embodiment of the present invention.
Figure 8D:
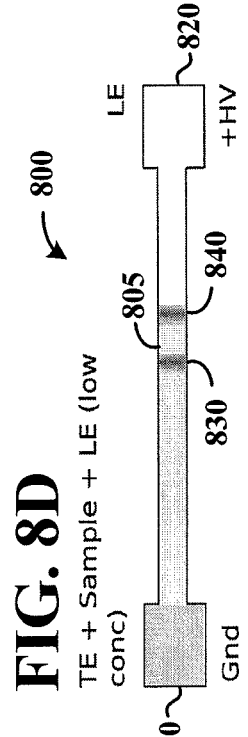
Figure 8A:
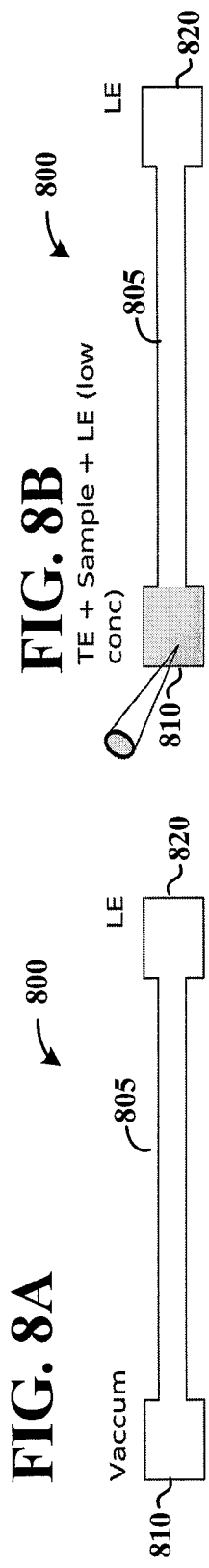
Figure 8C:
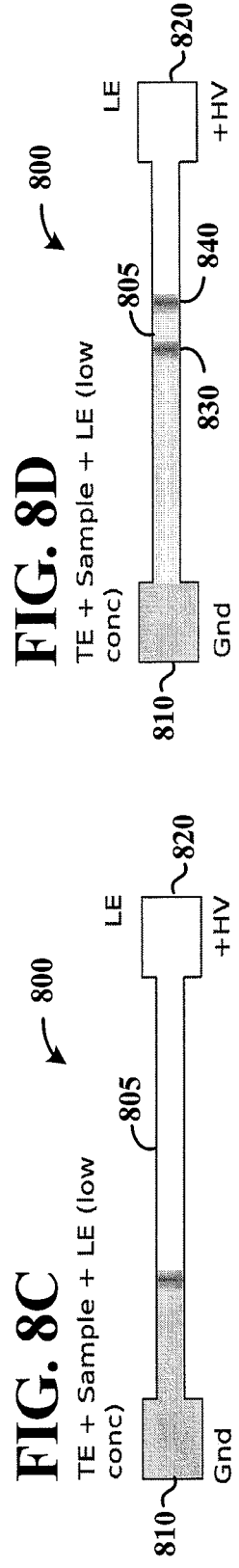

At FIG. 8B, the west well 810 is rinsed and filled with mixture of trailing electrolyte, samples and a relatively low concentration of leading electrolyte (e.g., leading electrolyte having a concentration of about 10-100-fold lower than trailing electrolyte). At FIG. 8C, an electric field is applied across the separation channel 805 to initiate isotachophoretic stacking by applying a high voltage at the east well 820. The leading ions are faster in response to the electric field, relative to the trailing ions, and overspeed the trailing and sample ions. As shown in FIG. 8D, the leading ions break the isotachophoretic mode and induce separation of samples 830 and 840.

FIGS. 9A-9D show a single-channel electrophoresis arrangement 900 and approach at various stages, according to another example embodiment of the present invention. The arrangement 900 includes west and east wells 910 and 920 at opposite ends of a separation channel 905. At FIG. 9A, the arrangement 900 is filled with leading electrolyte material having at least one counterion material that is a strong base/acid, by application via one or both wells 910 and 920 and pressure-driven flow to fill the separation channel 905. Strong bases and acids that may be used in connection with this example embodiment include, for example, sodium as strong base or chloride as strong acid.

Figure 9A:
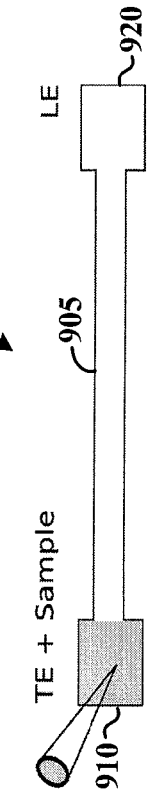
FIGS. 9A-9D show a single-channel electrophoresis arrangement and approach at various stages, according to another example embodiment of the present invention.
Figure 9B:
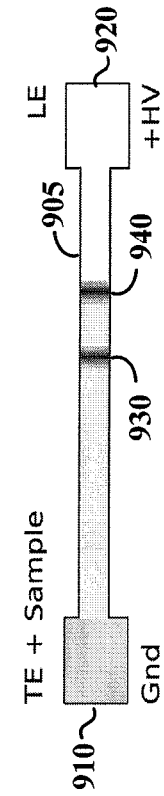
Figure 9C:
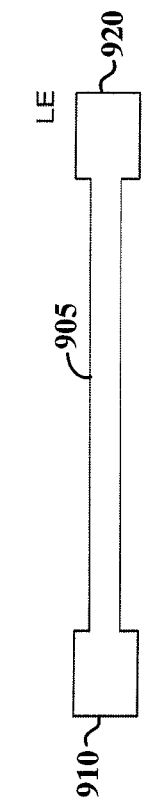
Figure 9D:
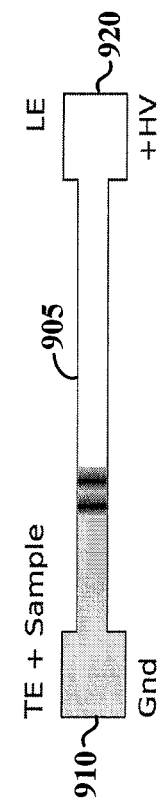

At FIG. 9B, the west well 910 is rinsed and filled with a mixture of trailing electrolyte material and sample ions. The trailing electrolyte material includes a weak acid/base co-ion material having an electrophoretic mobility that is lower than the sample ions when partially dissociated and higher than the sample ions when fully dissociated. At FIG. 9C, an electric field is applied across the separation channel 905 by applying a high voltage at the east well 920 and grounding the west well 910. The influx of strong electrolyte ions from the leading zone into the weak electrolyte trailing zone is used to increase the effective mobility of the trailing ions. The trailing ions thus respond to the applied electric field by overspeeding the sample ions to break the isotachophoresis mode and induce separation of samples 930 and 940 as shown in FIG. 9D.

Figure 10:
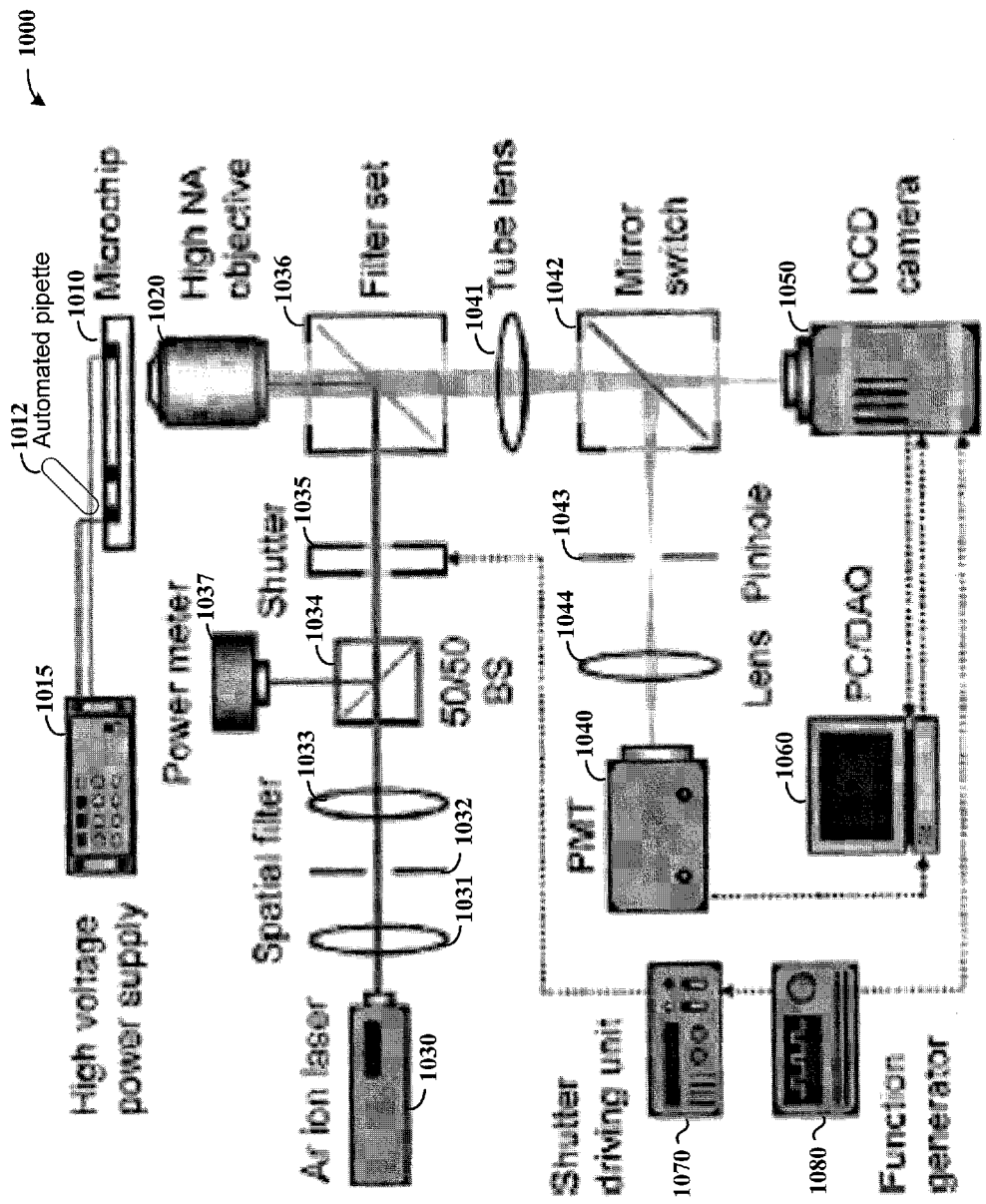
FIG. 10 shows a system for high-sensitivity on-chip ITP/CE, according to another example embodiment of the present invention.

FIG. 10 shows a system 1000 for high-sensitivity on-chip ITP/CE, according to another example embodiment of the present invention. This system 1000 may, for example, be used to implement one or more of the example embodiments and approaches discussed herein. The system 1000 includes a microchip arrangement 1010 having a microchannel, such as a T-microchannel, cross-microchannel or single-channel (e.g., generally linear) microchannel as described above. A high voltage power supply 1015 is electrically coupled to the microchip to apply a voltage to the microchannel to facilitate sample separation, such as by using one of the ITP/CE type approaches as described above.

An objective 1020 is arranged relative to the microchip arrangement 1010 to image separated samples. A laser 1030 (here, an Argon ion laser by way of example) supplies light through the objective to illuminate the sample, via optical components 1031, 1032 and 1033, a beam splitter 1034 that directs light to a power meter 1037, a shutter 1035 and a filter set 1036. The shutter 1035 is driven by a shutter driving unit 1070, which generates a driving signal in response to a function generator 1080.

The objective 1020 passes light from the sample in the microchip to one of a photomultiplier tube 1040 and a ICCD (intensified CCD) camera 1050, via the filter set 1036, a tube lens 1041 and a mirror switch 1042 that selectively passes the light to one (or both) of the photomultiplier tube and the ICCD camera. Light passed to the photomultiplier tube is also passed through a pinhole 1043 and lens 1044, after being directed from the mirror switch 1042. The ICCD camera 1050 is operative using a signal from the function generator 1080.

Both the photomultiplier tube 1040 and the ICCD camera 1050 pass output data characterizing detected light to a data acquisition computer 1060. The computer 1060 processes the information and makes data available for analysis of samples in the microchip 1010.

In some embodiments, the system 1000 further includes an automated pipette arrangement 1012 to add one or more of electrolytes and samples to the microchip 1010. For example, in some applications, the automated pipette arrangement 1012 is used to add additional leading electrolyte (LE) material to a well in the microchip 1010, after samples therein have been isotachophoretically stacked; the additional LE is used to mitigate isotachophoretic stacking and facilitate capillary electrophoresis. In other applications, the automated pipette arrangement 1012 is used to add initial LE, a mixture of samples and trailing electrolytes, or other material to the microchip 1010. For certain applications, the automated pipette arrangement 1012 is coupled to the computer 1060 and controlled by the computer for automatically adding material to the microchip 1010.

Figure 11A:
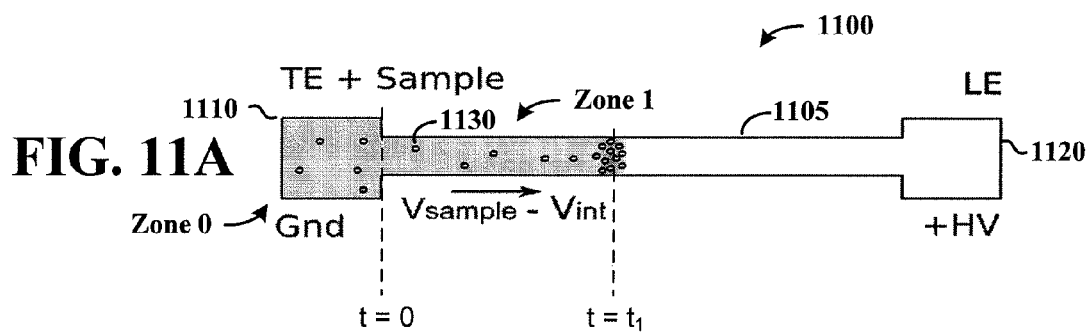
Figure 11B:
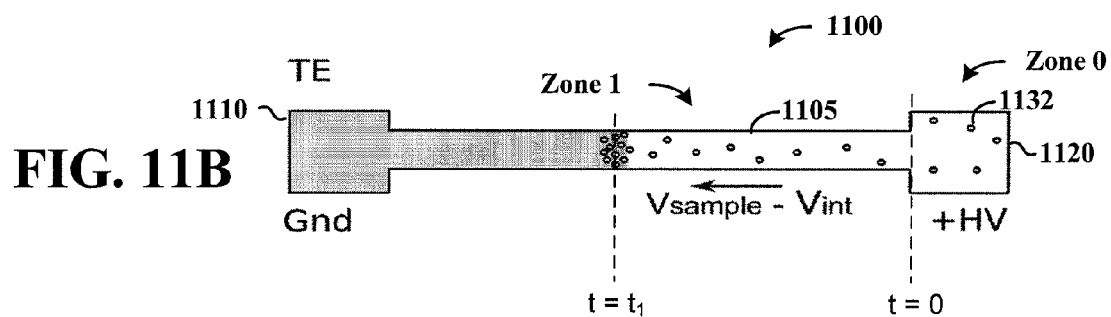
Figure 11C:
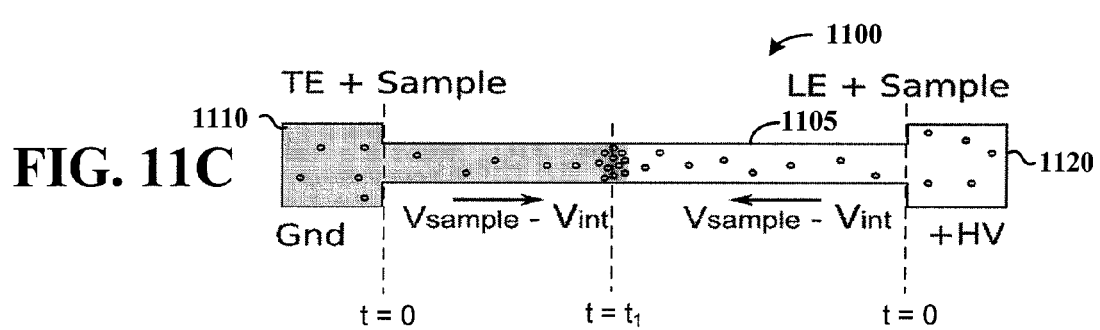

In various embodiments, some of which are described above, a sample undergoing analysis is mixed with leading electrolytes (LE), trailing electrolytes (TE), or with both leading and trailing electrolytes (i.e., separately, prior to introduction to a microchannel). FIGS. 11A-11C show a single-channel arrangement 1100 with three such approaches for isotachophoretic separation, according to various example embodiments. The arrangement 1100 includes a main separation channel 1105 and west and east reservoirs 1110 and 1120, respectively. In each embodiment, the samples are focused at the interface of LE and TE. The rate of focusing is set via the electrophoretic mobilities of the sample species and the concentration of LE and TE (with the concentration of the sample being significantly less than that of the LE and TE, such as consistent with the embodiments described above).

Turning to FIG. 11A, LE are added to the east reservoir 1120 and sample ions are mixed with TE and added to the west reservoir 1110, and the samples are separated using an isotachophoretic (ITP) preconcentration approach in connection with another example embodiment of the present invention. Samples are represented by small round circles with sample ion 1130 labeled by way of example. At time t=0, a voltage is applied across the microchannel arrangement, with the west reservoir 1110 grounded and a high voltage applied at the east reservoir 1120. Here, the LE and TE boundary move at nearly the same speed as sample ions are isotachophoretically moved into the sample zone 1.

The net influx of sample ions into the sample zone 1=$(v_s - v_T)E_T C_{s,TE1}$ $$1 = (v_s - v_T)E_T C_{s,TE1} = \left(\frac{v_s}{v_T} - 1\right) v_T E_T C_{s,TE1} \quad (1)$$
$$= \left(\frac{v_s}{v_T} - 1\right) v_L E_L C_{s,TE1}.$$

The velocity of the sample ions with respect to the interface is in a direction from the west reservoir 1110 towards the east reservoir 1120, as represented by the example arrow below the main separation channel 1105. At time $t=t_1$, the samples have concentrated as shown, at a boundary or interface between the mixture of TE and sample and the LE.

FIG. 11B shows ITP preconcentration with sample ions mixed with leading electrolyte and added to the microchannel arrangement 1100 at the east reservoir 1120, in connection with another example embodiment of the present invention. As with FIG. 11A, the samples are represented by small circles, with sample 1132 labeled by way of example. At time $t=0$, a high voltage is applied to the east reservoir 1120, and the west reservoir 1110 is grounded. The velocity of the sample ions with respect to the interface is represented by the example arrow below the main separation channel 1105, moving from the east reservoir 1120 towards the west reservoir 1110 in the main separation channel. The samples are concentrated at a boundary between the samples and TE at time $t=t_1$ as shown.

The net influx of sample ions into the sample zone (zone 1)$=(v_L-v_S)E_L C_{s,LE}$ $$(\text{zone } 1) = (v_L - v_S)E_L C_{s,LE} = \left(1 - \frac{v_s}{v_L}\right) v_L E_L C_{s,LE} \quad (2)$$

The accumulation rate of sample ions in the embodiments shown in FIG. 11A and FIG. 11B is different; the two equations (1) and (2) would be identical if $$\left(\frac{v_s}{v_T} - 1\right) C_{s,TE1} = \left(1 - \frac{v_s}{v_L}\right) C_{s,LE} \quad (3)$$

$C_{S,TE1}$ is the sample ion concentration in the regulated TE zone (behind the LE zone), and is related to initial sample concentration as:

$$C_{S,TE1} = C_{S,TE,0} \frac{C_{TE,1}}{C_{TE,0}} \quad (4)$$

where, $C_{TE0}$ is the initial TE concentration and $C_{TE1}$ is the regulated TE concentration behind LE, given by:

$$C_{TE,1} = C_{LE}\left(\frac{v_T}{v_L}\right)\left(\frac{v_L + v_A}{v_T + v_A}\right) \quad (5)$$

Simplifying equation (3) results in:

$$v_s = \frac{v_L v_T(1+k)}{(v_L + k v_T)}, \text{ where} \quad (6)$$

$$k = \frac{C_{S,LE}}{C_{S,TE1}} = \frac{C_{TE,0}}{C_{LE}}\left(\frac{v_L}{v_T}\right)\left(\frac{v_T + v_A}{v_L + v_A}\right) \quad (7)$$

If $C_{TE,0}=C_{TE,1}$, then $k=1$ and $v_S$ is the harmonic mean of $v_{TE}$ and $v_{LE}$ In view of the above equations 1-7, and in connection with various example embodiments, a sample or samples are analyzed using a mixture of the sample with one of TE or LE in accordance with the following:

(a) If $v_{sample} > v_S$, the sample ion is added to the TE as shown in FIG. 11A, where $v_S$ is given by equation (6); and (b) If $v_{sample} < v_S$, the sample ion is added to the LE as shown in FIG. 11B, where $v_S$ is given by equation (6).

In certain embodiments, a sample is separately mixed with both LE and TE as shown in FIG. 11C. In a manner similar to that described above in connection with each of FIGS. 11A and 11B, a mixture of a sample with TE is added to the west reservoir 1110, and a mixture of the sample with LE is added to the east reservoir 1120. At time $t=0$, a high voltage is applied to the east reservoir 1120 with the west reservoir grounded. This applied voltage (electric field) across the main separation channel 1105 facilitates the ITP movement and concentration of sample ions from each reservoir at the interface or boundary near the middle of the separation channel 1105 at time $t=t_1$ as shown.

Under the following two headings, an electromigration model and scaling are described with dispersion rates, summarizing the salient physics of ITP and used here to characterize ITP processes as described herein (by way of example). These approaches may, for example, be implemented in connection with one or more example embodiments as described herein, in connection with the figures and otherwise.

Figure 12A:
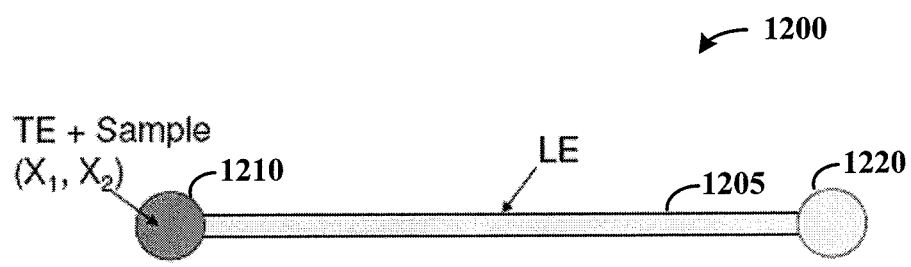
FIGS. 12A-12C show steps in an approach for single-channel sample separation via reverse polarization, according to another example embodiment of the present invention.

FIG. 12 shows steps in an approach for sample separation in a single-channel microchannel 1200 using reverse polarization, according to another example embodiment of the present invention. Beginning with FIG. 12A, the microchannel arrangement 1200 includes a separation channel portion 1205 and opposing west and east reservoirs 1210 and 1220 that are amenable to voltage application. Leading electrolyte is filled in the separation channel 1205 and east reservoir 1220, and a mixture of trailing electrolyte and samples ($X_1$ and $X_2$) is filled in the west reservoir 1210.

Figure 12B:
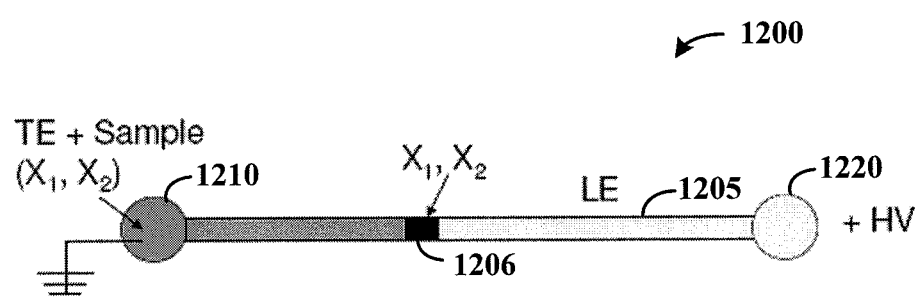
Figure 12C:
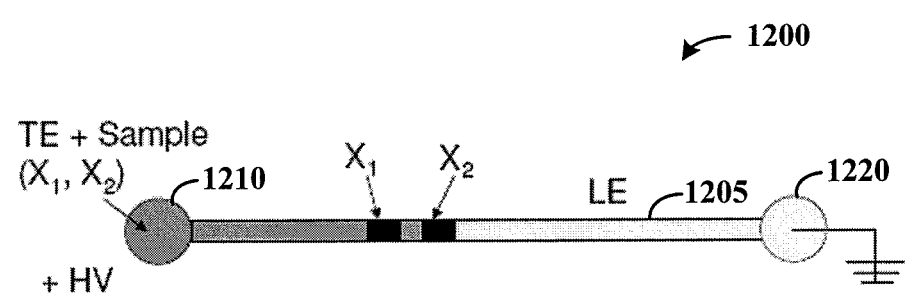

At FIG. 12B, a voltage is applied across the microchannel arrangement 1200, with the west reservoir 1210 grounded and a voltage applied to the east reservoir 1220, to facilitate isotachophoretic stacking of the samples as shown at portion 1206 of the main separation channel 1205. At FIG. 12C, the polarity of the voltage applied to the microchannel arrangement 1200 has been reversed, with a voltage applied to the west reservoir 1210 and the east reservoir 1220 grounded. This voltage application facilitates an overspeeding of the leading electrolytes past trailing electrolytes at the samples, towards the west reservoir 1210. This overspeeding in turn facilitates the separation of the samples $X_1$ and $X_2$ as shown.

Non-Dispersive One-Dimensional Electromigration

The following describes a one-dimensional (1D) non-diffuse ion species approach for ITP focusing, as applicable for one or more example embodiments. The general transport of ions is governed by a conservation law for dilute species, $$\frac{\partial C_i}{\partial t} + \vec{u} \cdot \vec{\nabla} C_i = -v_i \vec{\nabla} \cdot \left(C_i \vec{E}\right) + D_i \nabla^2 C_i \quad (1A)$$

where $C_i$ is the molar concentration of ion i, $v_i$ is the electrophoretic mobility, and E is the electric field. The following scales are used for nondimensionalization: [C]=$C_0$, [t] $v_0E_0$, [$\vec{u}$]=–$\epsilon\zeta_0E_0/\mu$, [L]=w, [$v_i$]=$v_0$, [$\vec{E}$]=$E_0$, [$D_i$]=$D_0$; where $v_0$, $\zeta_0$, $D_0$, and $\delta$ are respectively the characteristic scales for electrophoretic mobility, zeta potential, diffusivity, and stacked sample zone length. The dimensionless equation is then $$\frac{\partial C_i}{\partial t} + \alpha \vec{u} \cdot \vec{\nabla} C_i = -v_i \vec{\nabla} \cdot (C_i \vec{E}) + \frac{1}{Pe} D_i \nabla^2 C_i. \quad (2A)$$

The parameters are defined as Pe=$E_0v_0\delta/D_0$ and $\alpha$=–$\epsilon\zeta_0/(\mu v_0)$. Pe is the electric Peclet number, a measure of the ratio of diffusion time to electromigration time and $\alpha$ is the ratio of electroosmosis to electrophoretic mobility.

In the case of large Pe and small $\alpha$, a high E exists with suppressed electroosmotic mobility where both diffusion and advective dispersion are negligible compared to the effects of electromigration, so that $$\frac{\partial C_i}{\partial t} + v_i \vec{\nabla} \cdot C_i E = 0. \quad (3A)$$

Multiplying Equation (3A) by $z_i/v_i$ and summing over all species gives $$\frac{\partial}{\partial t}\left(\sum_i \frac{z_i C_i}{v_i}\right) + \nabla \cdot \left(E\sum_i z_i C_i\right) = 0 \quad (4A)$$

where $z_i$ is the valence number. The electroneutrality approximation requires the sum of products of concentrations and valences of ionic species must be zero so that $$\sum z_i C_i = 0.$$

Equation (4A) then becomes $$\sum_i \frac{z_i C_i}{v_i} = f(x). \quad (5A)$$

This is the well-known Kohlrausch regulating function, which suggests that sample concentration fields are constrained by the initial multi-species concentration profile.

One embodiment is directed to a model ITP system including a leading ion, LE$^-$, sample ion, S$^-$, a trailing ion, TE$^-$, and common counter ion, A$^+$ as implemented with the schematic concentration plot in FIG. 1A, with one sample ion considered here by way of example. After ITP stacking, the interface between the sample and LE zones migrates at the same velocity so $v_{LE}E^R=v_SE^L$ (superscripts R and L denote the right-hand and left-hand zones, respectively). From electroneutrality, $C_A^R-C_{LE}^R=0$ and $C_A^L-C_S^L=0$, and electric current density, i, should be uniform along the direction of applied electric field: $i=\sigma^R E^R=\sigma^L E^L$. Here $\sigma$ is the electrical conductivity of the solution, $$\sigma = F \sum |v_i| C_i.$$

The following expression is obtained from Equation 5A for concentration adjustment between the two zones in this ITP example $$C_{S,final} = C_{LE}^R \frac{v_S(v_A + |v_{LE}|)}{v_{LE}(v_A + |v_S|)}. \quad (6A)$$

Here, the adjusted sample concentration, $C_{S,final}$, is only a function of the LE concentration and electrophoretic mobilities (and not a function of, for example, TE concentration).

The degree of stacking in this simple ITP process can be characterized in terms of concentration increase, CI or signal increase, SI. CI refers to stacked sample concentration divided by the original sample concentration. SI refers to the ratio of the signal detected with sample preconcentration (e.g., at some downstream location after an electrophoretic separation) to the signal obtained without stacking. For the current model, CI=$C_{S,final}/C_{S,initial}$ where $C_{S,final}$ is given by Equation 6A. In this regard, CI increases in direct proportion with LE concentration, and CI is inversely proportional to initial sample concentration. Using this approach, an ITP analysis approach can be implemented and/or analyzed (e.g., for expected implementation or otherwise), in accordance with one or more example embodiments herein.

ITP Approaches: Scaling of Dispersion Rates

In this section, scaling approaches are described that, together with the non-dispersive 1D electromigration model above, are used in implementing ITP for a variety of approaches, in connection with one or more example embodiments. The non-dispersive approach above neglects the effects of molecular diffusion and convective dispersion on stacked sample concentration, where the term dispersion is used to refer to both molecular diffusion and convective dispersion. ITP has gradients of ion density and species mobility, which leads to axial gradients in electric field, and gradients of electrophoretic velocities of ionic species and electroosmotic velocity of bulk liquid. Electroosmotic velocity gradients are particularly useful in determining dispersion. For any two regions of the channel, the electroosmotic velocity mismatch can be expressed as $$\frac{U_{eo,1}}{U_{eo,2}} = \frac{\zeta_1 E_1}{\zeta_2 E_2} \cong \gamma^{-1+b}, \quad (7A)$$

where $U_{eo,1}$ and $U_{eo,2}$ are the electroosmotic velocity of the two regions (e.g., in practical ITP, the regions containing LE and TE). In each channel region, $U_{eo}$ is determined by the applied electric field, local conductivity, and the local value of electroosmotic mobility. The rightmost term in Equation 8A below shows one example term used this velocity ratio where $\gamma$ is the electrical conductivity ratio of the two zones, and b represents zeta potential ($\zeta$) dependence on the concentration of electrolyte ($\zeta \sim C^b$) (the –1 term in the exponent captures the inverse dependence of conductivity on ion density). The value of b depends on the chemistry of the channel surface and the electrolyte solution; a typical range is between –0.2 and –0.3. This mismatch in EOF velocity generates a pressure gradient that causes sample dispersion and lowers stacking efficiency.

In the limit of negligible EOF velocities (i.e., perfectly suppressed EOF), the dominant source of dispersion in ITP will be molecular diffusion. A sample ion Peclet number is characterized in terms of the electrophoretic velocity of the sample and the width of the stacked sample zone, $$Pe_s = \frac{E_\delta v_s}{D}\left(\frac{l}{CI}\right) \quad (8A)$$

Here $E_\delta$ is the local electric field (in the stacked sample zone), D is the molecular diffusion coefficient of the sample ions, l is the effective initial length of the region of sample to be stacked, and CI is the stacking ratio, in general $CI=C_{S,final}/C_{S,initial}$. CI scales as $1/\delta$, where $\delta$ is the length scale of the stacked sample zone. This $Pe_s$ can be used to compare relative importance of electromigration (which leads to sample stacking) and diffusion (which works against sample stacking). Equation 8A therefore suggests that large $E_\delta$ and large l lead to better stacking, two qualitative trends we observe in practice. $E_\delta$ is a function of applied field and the conductivities of the sample, LE, and TE zones. For example, for a given applied total potential, low TE concentration increases $E_\delta$ and is used to facilitate stacking.

In some applications, the term l is increased by injecting large, finite sample plugs. In other applications, the effective value of l is increased by setting up a single interface ITP process (e.g., as shown in the inset of FIG. 1A). In this single interface configuration, the sample is initially uniformly dissolved into the TE and stacking is achieved in a zone between the TE and LE (e.g., as shown in FIGS. 1B, 1C and 1D). In this approach, the effective injected sample plug length is not limited by channel length but by the amount of sample that can flow into the channel (e.g., from the reservoir) and by the length between the injection region and the detector (which limits the time of stacking). In single interface ITP, sample concentration first increases and then saturates at a "fully stacked" value. The width of the stacked sample region then increases indefinitely (albeit very slowly). For low initial sample concentration and high LE concentration (a case of interest), the local field in the TE zone is related to the (growing) length of the TE zone and TE ion concentration. The relatively low conductivity TE zone is a high resistance in series with the rest of the channel. In various applications, TE concentration and TE zone length also strongly affects the stacked sample zone electric field, $E_\delta$.

EXPERIMENTAL DATA

The following describes approaches that may be implemented in connection with one or more example embodiments of the present invention.

In one application, N-hydroxyethylacrylamide (HEA) (e.g., available from Cambrex Bio Science (Walkersville, Md.) and V-50 initiator (2,2'-azobis (2-amidinopropane) dihydrochloride) (e.g., available from Wako Chemical USA (Richmond, Va.) are used in an integrated ITP/CE approach. Polymers of HEA are synthesized using free-radical polymerization in aqueous solution. Alexa fluor 488 and bodipy (available from Molecular Probes of Eugene, Oreg.) are used as sample analytes. Rhodamine B (Acros Organics, Morris Plains, N.J.) are used as a neutral marker to quantify EOF. Sodium chloride, sodium hydroxide, and hydrochloric acid are also used (e.g., available from Fisher Scientific of Pittsburgh, Pa.). Each of TE and LE respectively include 5 mM HEPES (pH 7.0; available from Sigma of St. Louis, Mo.) titrated with sodium hydroxide, and 1 M NaCl dissolved in deionized water. HEPES ions, chloride ions, and sodium ions are used as the trailing ion, leading ion and counter ion, respectively. About 0.1% w/v poly-N-hydroxyethylacrylamide (PHEA) is added to the electrolytes to suppress EOF. The electrolyte solutions are filtered prior to use with 200 nm pore syringe filters (e.g., available from Nalgene Labware of Rochester, N.Y.).

A standard, cross-pattern glass microchip (e.g., available from Micralyne of Alberta, Canada) is used with channels 50 µm wide and 20 µm in depth. Images of the sample injection, stacking, and separation process are captured with an inverted epifluorescent microscope IX70 with 4× (N.A. of 0.16), 10× (N.A. of 0.4), and 20× (N.A. of 0.5) objectives (available from Olympus of Hauppauge, N.Y.) and an XF100-3 filter cube (e.g., available from Omega Optical of Brattleboro, Vt.) with peak excitation and emission wavelength ranges of 450-500 nm and 500-575 nm, respectively. Images are recorded using a generation III, intensified CCD camera (e.g., the IPentaMAX available from Roper Scientific of Trenton, N.J.) with a 12-bit intensity digitization resolution. A LabVIEW-controlled high voltage power supply (Micralyne, Alberta, Canada) is used to control the electric field for ITP/CE process.

While the present invention has been described above and in the claims that follow, those skilled in the art will recognize that many changes may be made thereto without departing from the spirit and scope of the present invention. Such changes may include, for example, implementing T-channel approaches with cross channels, implementing cross channel approaches with T-channels, implementing these approaches with other channel types, or integrating other electrophoretic approaches with the isotachophoretic approaches discussed herein. These and other approaches as described in the contemplated claims below characterize aspects of the present invention.

What is claimed is:

1. A method for electrophoretic analysis, the method comprising
   in a microchannel, forming an interface between first electrolytes and an electrolyte-sample mixture, the mixture having at least one type of sample analytes mixed with second electrolytes prior to addition to the microchannel, the electrophoretic mobility value of at least one type of the sample analytes being between the electrophoretic mobility values of the first and second electrolytes;
   isotachophoretically arranging the at least one type of sample analytes by applying an electric field to the microchannel;
   applying an electric field to the microchannel and exchanging the second electrolytes in the mixture with the first electrolytes to terminate isotachophoretic stacking; and
   detecting a characteristic of the arranged sample analytes and generating an output characterizing the detected characteristic wherein after the step of isotachophoretically arranging, electrolyte is added to the microchannel and an applied electric field effects the electrolyte exchange at the sample analytes with the added electrolyte.

2. The method of claim 1, further including electrophoretically arranging the at least one type of sample analytes, prior to detecting the characteristic, and wherein the step of isotachophoretically arranging includes using the applied electric field to concentrate the sample analytes.

3. The method of claim 1, wherein the electrolyte-sample mixture includes at least two types of sample analytes mixed in an electrolytic solution, further including electrophoretically separating the at least two types of sample analytes from one another, prior to detecting the characteristic.

4. The method of claim 1, wherein the electrolyte-sample mixture includes at least two types of sample analytes, further including electrophoretically separating the at least two types of sample analytes from one another, prior to detecting the characteristic, by electrophoretically replacing second electrolytes near the sample analytes with the first electrolytes to effect an electrolyte exchange that terminates isotachophoresis and initiates electrophoretic separation of the sample analytes.

5. The method of claim 1,
wherein the electrolyte-sample mixture includes at least two types of sample analytes,
wherein isotachophoretically arranging includes applying an electric field to preconcentrate a portion of the sample analytes via isotachophoresis and to isotachophoretically stack the preconcentrated sample analytes, and
further including separating the at least two types of sample analytes from one another via capillary electrophoresis.

6. The method of claim 1, wherein
one of the first and second electrolytes is a leading electrolyte having an electrophoretic mobility that is greater than the electrophoretic mobility of a particular type of the sample analytes, and
the other one of the first and second electrolytes is a trailing electrolyte having an electrophoretic mobility that is less than the electrophoretic mobility of said particular type of the sample analytes.

7. The method of claim 1, wherein the microchannel is a capillary.

8. The method of claim 1, wherein the microchannel is in a microchip.

9. The method of claim 1, further including treating the microchannel to suppress electroosmotic flow, prior to forming an interface.

10. The method of claim 1, wherein the first electrolytes and the sample analytes in the microchannel have a relative molar ratio of first electrolytes to sample analytes that is at least about 1000:1.

11. The method of claim 1, wherein applying an electric field includes applying an electric field having a high local gradient that is greater than about 200 V/cm.

12. The method of claim 1, further including, after isotachophoretically arranging the at least one type of sample analytes, adding electrolyte to the microchannel and applying an electric field to the microchannel to effect the electrolyte exchange at the sample analytes with the added electrolyte.

13. The method of claim 1, wherein forming an interface includes using pressure-driven flow to form the interface.

14. The method of claim 1, wherein forming an interface includes pipetting the electrolyte-sample mixture into the microchannel.

15. The method of claim 1, wherein the electrolyte-sample mixture includes the first electrolytes, second electrolytes and at least two types of sample analytes, further including effecting the electrolyte exchange at said sample analytes by overspeeding said second electrolytes with said first electrolytes in said mixture via application of an electric field to said mixture in the microchannel.

16. The method of claim 1, wherein at least one the first electrolytes and the electrolyte-sample mixture includes a linear polymer material to suppress electroosmotic flow.

17. A method for single-channel electrophoresis, the method comprising:

adding leading electrolyte material to a single-channel microchannel;
adding a mixture including a trailing electrolyte material and at least two samples to the microchannel, the electrophoretic mobilities of the leading and trailing electrolyte materials being respectively larger and smaller than the electrophoretic mobilities of the samples;
isotachophoretically stacking the samples by applying an electric field to the microchannel; and
separating the stacked samples by applying an electric field to the microchannel to exchange the trailing electrolyte material in the sample with the leading electrolyte material, to mitigate the isotachophoretic stacking and facilitate capillary electrophoresis of the stacked samples with the leading electrolytes.

18. The method of claim 17, wherein adding leading electrolyte material includes adding leading electrolyte material, after isotachophoretically stacking the samples, and before applying an electric field to electrophoretically move the leading electrolytes.

19. The method of claim 17, wherein
adding a mixture includes adding a mixture that includes the trailing electrolyte material, the at least two samples and said leading electrolyte material to the microchannel, and
isotachophoretically stacking the samples and separating the stacked samples include continuously applying an electric field to first isotachophoretically stack the samples and subsequently separate the stacked samples.

20. The method of claim 17, wherein
adding leading electrolyte material includes adding at least one counterion material that is a strong base or acid,
adding a mixture includes adding a mixture of the at least two samples in solution with a trailing electrolyte material solution having a weak acid/base co-ion trailing electrolyte material with an electrophoretic mobility that is lower than the samples when partially dissociated and higher than the samples when fully dissociated, and
separating the stacked samples includes applying an electric field to move the counterion material into the trailing electrolyte material to dissociate and increase the effective mobility of the trailing electrolyte material, thereby causing the trailing electrolyte material to overspeed the samples to mitigate isotachophoretic stacking and initiate separation of the samples.

21. The method of claim 17, wherein
adding leading electrolyte material includes adding leading electrolyte material to the microchannel before adding the mixture, and
isotachophoretically stacking the samples and separating the stacked samples include isotachophoretically stacking the samples and separating the stacked samples in the mixture without adding any leading electrolyte material to the microchannel after adding the mixture.

22. The method of claim 17, wherein
adding leading electrolyte material includes adding leading electrolyte material to the microchannel before adding the mixture, and
adding a mixture includes adding a mixture including additional leading electrolyte material.

23. The method of claim 17, wherein adding a mixture includes adding a mixture including leading electrolyte material at a concentration that facilitates, in response to said applied electric field,
the isotachophoretic stacking,
the subsequent mitigation of the isotachophoretic stacking, and the separation of the at least two samples via capillary electrophoresis.

24. The method of claim 17, wherein isotachophoretically stacking and separating the stacked samples include applying an electric field by grounding an end of the microchannel and applying a voltage to an opposite end of the microchannel.

25. The method of claim 17, wherein separating the stacked samples includes applying an electric field having a polarity that is opposite the polarity of the electric field applied at the step of isotachophoretically stacking.

26. A method for analyzing sample analytes in a T-microchannel having a main separation channel, a side channel and a reservoir connected to an upstream portion of the main separation channel, the method comprising:
 introducing first electrolytes into a downstream portion of the main separation channel, the electrophoretic mobility of the first electrolytes being larger than the electrophoretic mobility of the sample analytes;
 introducing a mixture of second electrolytes with the sample analytes into an upstream portion of the main separation channel using pressure driven flows and forming a boundary between the first and second electrolytes at an intersection of the T-microchannel, the electrophoretic mobility of the second electrolytes being less than the electrophoretic mobility of the sample analytes;
 applying a voltage difference between the downstream and the upstream portion of the main separation channel to isotachophoretically stack the sample analytes; and
 after applying the voltage difference, filling the reservoir with electrolytes of the first electrolyte type and again applying a voltage difference between the downstream and the upstream portion of main separation channel to separate the sample analytes.

27. The method of claim 26, wherein filling the reservoir with electrolytes of the first electrolyte type and again applying a voltage difference between the downstream and the upstream portion of main separation channel to separate the sample analytes includes causing the electrolytes filled in the reservoir to overtake the sample analytes, effecting an electrolyte exchange at the sample analytes that terminates isotachophoretic stacking and initiates capillary electrophoresis separation.

28. The method of claim 26, further including treating the microchannel to suppress electroosmotic flow, prior to introducing the first electrolytes and the mixture to the microchannel, wherein
 introducing the first electrolytes and introducing the mixture include introducing the first electrolytes and the sample analytes at a molar ratio of electrolytes to analytes (electrolytes:analytes) of about $10^{15}$:1, and
 the steps of applying a voltage difference include applying an electric field of greater than about 200V/cm to the microchannel.

29. A single-interface electrophoresis method for analyzing a sample in a single-channel microchip microchannel having a single main separation channel with wells at opposite ends thereof, the method comprising:
 filling the separation channel with the leading electrolytes;
 introducing a mixture including trailing electrolytes mixed with at least two types of sample analytes into one of said wells and forming a single interface between the mixture and the leading electrolytes, the electrophoretic mobility of sample analytes being higher than the trailing electrolytes and lower than the leading electrolytes;
 applying an electric field to the separation channel to initiate isotachophoretic stacking of the at least two types of sample analytes; and
 after isotachophoretically stacking the at least two types of sample analytes, applying an electric field across the separation channel to facilitate overspeeding of the sample analytes by an electrolyte to
 mitigate said isotachophoretic stacking, and
 electrophoretically separate the at least two types of sample analytes via capillary electrophoresis.

30. A system for single-channel electrophoresis, the system comprising:
 a separation channel arrangement having first and second wells and electrodes at opposing ends and a single uninterrupted separation channel connecting the opposing ends;
 in the single separation channel, a first electrolyte material and a homogeneous mixture including a second electrolyte material and at least one sample, the electrophoretic mobility of at least one of the at least one sample having a value that is between the respective electrophoretic mobility values of the first and second electrolyte materials; and
 a voltage supply configured and arranged with the electrodes and separation channel to apply an electric field to the separation channel via the electrodes to isotachophoretically stack the at least one sample, wherein the separation channel arrangement includes a single interface between the homogeneous mixture and the first electrolyte material and wherein the sample is located simultaneously in one of the wells in the separation channel arrangement and in a region between the first and second electrolyte material.

31. The system of claim 30, wherein the voltage supply is further configured and arranged to apply an electric field to the separation channel with each of the first and second wells being configured with an electrode in the separation channel arrangement to separate the stacked samples by mitigating the isotachophoretic stacking and facilitating capillary electrophoresis of the stacked samples.

32. The system of claim 30, further including an automated pipette configured and arranged to add at least one of the first electrolyte material and the mixture to the separation channel, wherein the voltage supply is further configured and arranged to apply an electric field to the separation channel with each of the first and second wells being configured with an electrode in the separation channel arrangement.

33. The system of claim 30, further including an automated pipette configured and arranged to add additional electrolyte material to an upstream portion of the separation channel, after the application of the electric field to isotachophoretically stack the at least one sample, wherein the voltage supply is further configured and arranged to apply an electric field to separate the stacked at least one sample by applying the electric field to move the additional electrolyte material downstream to the at least one sample to mitigate the isotachophoretic stacking and facilitate the capillary electrophoresis, wherein each of the first and second wells is configured with an electrode in the separation channel arrangement.

34. A method for single-channel isotachophoresis, the method comprising:
 adding a first electrolyte material to a single-channel microchannel;
 adding a mixture including a second electrolyte material and a sample to the microchannel, the electrophoretic mobility of the sample having a value that is between the respective electrophoretic mobility values of the first and second electrolyte materials;

isotachophoretically concentrating the sample by applying an electric field to the microchannel;

applying an electric field to the microchannel and exchanging the second electrolyte material in the mixture with the first electrolyte material to terminate isotachophoretic stacking; and analyzing the concentrated sample.

35. The method of claim 34, further including forming a single interface between the mixture and the first electrolyte material, prior to isotachophoretically concentrating the sample.

36. The method of claim 34, wherein adding a mixture including a second electrolyte material and a sample to the microchannel includes adding a mixture including the second electrolyte material and at least two samples in a liquid solution with the second electrolyte material to the microchannel, and isotachophoretically concentrating the sample by applying an electric field to the microchannel includes isotachophoretically stacking the at least two samples using the applied electric field, and analyzing the concentrated sample includes analyzing at least one of the isotachophoretically stacked samples.

37. The method of claim 34, wherein adding the first electrolyte material and adding the mixture include forming a single interface between the mixture and the first electrolyte material in the microchannel.

38. The method of claim 34, wherein adding the first electrolyte material and adding the mixture include adding a mixture including the first electrolyte material, the second electrolyte material and the sample to the microchannel.

39. The method of claim 34, wherein adding a first electrolyte material includes adding an electrolyte material having an electrophoretic mobility that is greater than the electrophoretic mobility of the sample, and adding a mixture including a second electrolyte material includes adding electrolyte material having an electrophoretic mobility that is less than the electrophoretic mobility of the sample.

40. The method of claim 34, wherein adding a first electrolyte material includes adding an electrolyte material having an electrophoretic mobility that is less than the electrophoretic mobility of the sample, and adding a mixture including a second electrolyte material includes adding electrolyte material having an electrophoretic mobility that is greater than the electrophoretic mobility of the sample.

41. The method of claim 34, further including adding a mixture including another sample having an electrophoretic mobility that has a value that is less than the respective electrophoretic mobility values of the first and second electrolyte materials.

42. The method of claim 34, further including adding a mixture including another sample having an electrophoretic mobility that has a value that is between the respective electrophoretic mobility values of the first and second electrolyte materials, isotachophoretically separating the samples, and wherein analyzing the concentrated sample includes analyzing the separated samples.

43. The method of claim 34, wherein isotachophoretically concentrating the sample by applying an electric field to the microchannel includes concentrating the sample using transient isotachophoresis.

44. A method for single-channel isotachophoresis, the method comprising:

adding a mixture including a first electrolyte material and a sample to a first end of a single-channel microchannel;

adding a mixture including a second electrolyte material and a sample to an opposite end of the microchannel, the electrophoretic mobility of the sample having a value that is between the respective electrophoretic mobility values of the first and second electrolyte materials;

isotachophoretically concentrating the sample by applying an electric field to the microchannel and isotachophoretically moving the samples at each end of the microchannel towards each other to combine the samples; and analyzing the combined samples.

45. A method for single-channel isotachophoresis, the method comprising:

adding a first electrolyte material to a single-channel microchannel;

adding a mixture including a second electrolyte material and a sample to the microchannel, the electrophoretic mobility of the sample having a value that is between the respective electrophoretic mobility values of the first and second electrolyte materials; and without adding any additional material to the microchannel, isotachophoretically concentrating the sample by applying an electric field to the microchannel, exchanging the second electrolyte material in the mixture with the first electrolyte material to terminate isotachophoretic stacking, and analyzing the concentrated sample.

* * * * *